United States Patent [19]

Hayashi et al.

[11] 4,110,341
[45] Aug. 29, 1978

[54] DITHIO PROSTAGLANDIN DERIVATIVES

[75] Inventors: Masaki Hayashi; Seiji Kori, both of Takatsuki; Hajimu Miyake, Suita, all of Japan

[73] Assignee: Ono Pharmaceutical Company, Osaka, Japan

[21] Appl. No.: 765,580

[22] Filed: Feb. 4, 1977

[30] Foreign Application Priority Data

Feb. 10, 1976 [GB] United Kingdom ............... 05145/76

[51] Int. Cl.² ........................................... C07D 339/04
[52] U.S. Cl. ............................ 260/327 C; 260/343.6; 260/456 R; 260/468 D; 260/514 D; 424/277; 424/305; 424/311; 560/106; 560/231; 260/346.22
[58] Field of Search ............. 260/327 C, 514 D, 340.6

[56] References Cited

U.S. PATENT DOCUMENTS

| | | | |
|---|---|---|---|
| 3,514,383 | 5/1970 | Beal et al. | 204/158 |
| 3,845,042 | 10/1974 | Strike et al. | 260/240 R |
| 3,931,296 | 1/1976 | Hayashi et al. | 260/514 D |
| 3,950,363 | 4/1976 | Bundy | 260/347.3 |

FOREIGN PATENT DOCUMENTS 68-03391  11/1968  South Africa ........................ 260/514 D

OTHER PUBLICATIONS

Corey et al., Tetrahedron Letters, #10, pp. 737–740, 1976.

*Primary Examiner*—Cecilla M. Jaisle
*Attorney, Agent, or Firm*—Albert H. Graddis; Frank S. Chow

[57] ABSTRACT

Prostaglandin analogues of the formula:

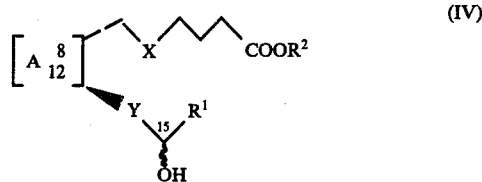

wherein A represents a grouping of the formula:

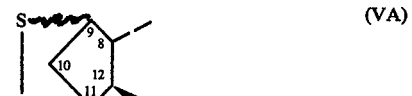

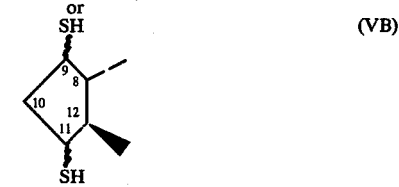

X represents ethylene or cis-vinylene, Y represents ethylene or trans-vinylene, $R^1$ represents a straight- or branched-chain alkyl group containing from 4 to 10 carbon atoms, and $R^2$ represents a hydrogen atom or a straight- or branched-chain alkyl group containing from 1 to 12 carbon atoms and cyclodextrin clathrates of such acids and esters and, when $R^2$ represents a hydrogen atom, non-toxic salts thereof, the bonds attaching the epidithio radical to the carbon atoms in the 9- and 11-positions in the grouping of formula VA being either botn in α-configuration or both in β-configuration are disclosed.

These compounds exhibit characteristic prostaglandin properties.

11 Claims, No Drawings

DITHIO PROSTAGLANDIN DERIVATIVES

THIS INVENTION is concerned with new prostaglandin analogues.

Prostaglandins are derivatives of prostanoic acid which has the following formula:

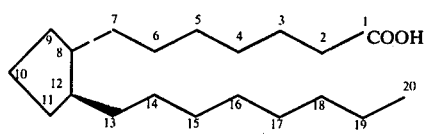

Various types of prostaglandins are known, the types depending inter alia on the structure and substituents on the alicyclic ring. For example, the alicyclic ring of prostaglandin F(PGF) has the structure:

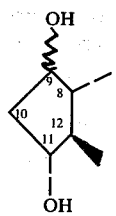

In the foregoing formulae and in other formulae throughout this specification the dotted lines denote, in accordance with generally accepted rules of nomenclature, that the attached grouping lies behind the general plane of the ring system, i.e. that the grouping is in α-configuration, the thickened lines
◥ denote that the grouping lies in front of the general plane of the system, i.e. that the grouping is in β-configuration, and the wavy line ∿∿ indicates that the grouping is in α- or β-configuration.

Such compounds are sub-classified according to the position of double bond(s) in the side chain(s) attached to the 8- and 12-positions of the alicyclic ring. Thus PG$_1$ compounds have a trans-double bond between C$_{13}$–C$_{14}$(trans-Δ$^{13}$) and PG$_2$ compounds have a cis-double bond between C$_5$–C$_6$ and a trans-double bond between C$_{13}$–C$_{14}$(cis-Δ$^5$, trans-Δ$^{13}$). For example, prostaglandin F$_{1α}$ (PGF$_{1α}$) is characterized by the following structure III.

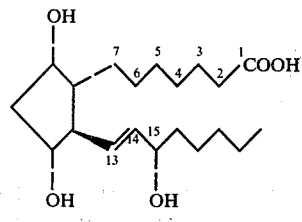

The structure of PGF$_{2α}$, as a member of the PG$_2$ group corresponds to that of formula III with a cis-double bond between the carbon atoms in positions 5 and 6. Compounds in which the double bond between the carbon atoms in positions 13 and 14 of members of the PG$_1$ group is replaced by ethylene are known as dihydro-prostaglandins, e.g. dihydro-prostaglandin-F$_{1α}$ (dihydro-PGF$_{1α}$).

Moreover, when one or more methylene groups are added to, or eliminated from, the aliphatic group attached to the 12-position of the alicyclic ring of the prostaglandins the compounds are known, in accordance with the usual rules of organic nomenclature, as homoprostaglandins (methylene group added) or nor-prostaglandins (methylene group eliminated), and, when more than one methylene group is added or eliminated, the number is indicated by di-, tri- etc. before the prefix "homo" or "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. As well as possessing the above-mentioned properties they sometimes cause undesirable effects such as production of fever, pain and inflammation. It is thought that prostaglandins are involved in the pyrexic and inflammatory responses in the living body. They are fat-soluble substances obtainable in very small quantities from various tissues of animals which secrete the prostaglandins in the living body.

During the past decade widespread investigations have been carried out in order to discover inter alia new products possessing the pharmacological properties of the 'natural' prostaglandins or one or more of such properties to an enhanced degree. It has now been found as a result of extensive research and experimentation that by replacing the hydroxy groups attached to the 9- and 11- position carbon atoms of prostaglandins F by an epidithio radical (—S—S—) or by thiol groups (—SH) new prostaglandin analogues are obtained which possess very weak or almost no activity in many of the pharmacological properties of the 'natural' prostaglandins, but possess strong platelet-aggregation-inducing and prostaglandin-biosynthesis-inhibiting activities which the 'natural' prostaglandins do not possess.

The present invention accordingly provides new prostaglandin analogues of the general formula:

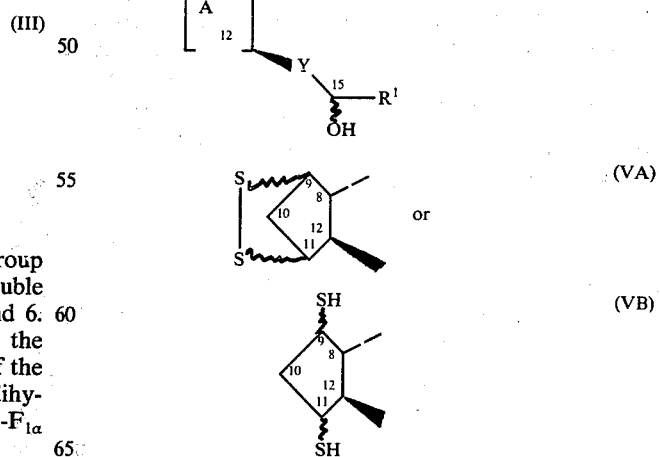

, X represents ethylene (i.e. —CH$_2$CH$_2$—) or, preferably, cis-vinylene (i.e. 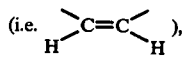), Y represents ethylene or, preferably, trans-vinylene (i.e. 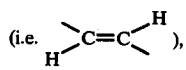), $R^1$ represents a straight- or branched-chain alkyl group containing from 4 to 10 carbon atoms, preferably n-pentyl, and $R^2$ represents a hydrogen atom or a straight- or branched-chain alkyl group containing from 1 to 12, preferably 1 to 4, carbon atoms, [e.g. methyl] and cyclodextrin clathrates of such acids and esters and, when $R^2$ represents a hydrogen atom, non-toxic salts thereof. The bonds attaching the epidithio radical to the carbon atoms in the 9- and 11-positions in the grouping of formula VA are either both in α-configuration or both in β-configuration. The hydroxy group attached to the carbon atom in the 15-position is preferably in α-configuration.

The present invention is concerned with all compounds of general formula IV in the 'natural' form or its enantiomeric form, or mixtures thereof, more particularly the racemic form consisting of equimolecular mixtures of natural and its enantiomeric form.

As will be apparent to those skilled in the art, the compounds depicted in general formula IV, wherein A represents a grouping of formula VA or VB, have at least five centres of chirality, these five centres of chirality being at the alicyclic ring carbon atoms identified as 8, 9, 11 and 12 and at the C-15 carbon atom which has attached to it a hydroxy group. The presence of chirality leads, as is well known, to the existence of isomerism. However, the compounds of general formula IV all have such a configuration that the side-chains attached to the ring carbon atoms in the positions identified as 8 and 12 are trans with respect to each other. Accordingly, all isomers of general formula IV, and mixtures thereof, which have those side-chains attached to the ring carbon atoms in positions 8 and 12 in the trans-configuration and have a hydroxy group as depicted in the 15-position are to be considered within the scope of general formula IV.

According to a feature of the present invention, the prostaglandin analogues of general formula IV, wherein A represents a grouping of formula VA and the bonds attaching the epidithio radical to the carbon atoms in the 9- and 11-positions are both in α-configuration, $R^2$ represents a hydrogen atom or a straight- or branched-chain alkyl group containing from 1 to 4 carbon atoms and the other symbols are as hereinbefore defined, i.e. compounds of the general formula:

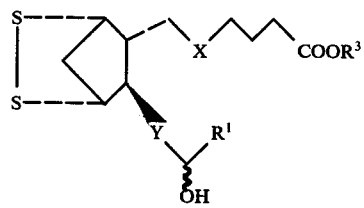

(IVA)

(wherein $R^3$ represents a hydrogen atom or a straight- or branched-chain alkyl group containing from 1 to 4 carbon atoms and the other symbols are as hereinbefore defined) may be prepared by the process which comprises the hydrolysis to a hydroxy group of the group $OR^4$ of an epidithio-cyclopentane derivative of the general formula:

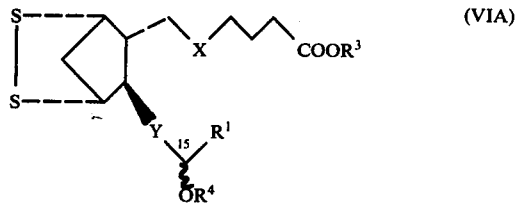

(VIA)

wherein $R^4$ represents a 2-tetrahydrofuranyl group, a 1-ethoxyethyl group or a 2-tetrahydropyranyl group unsubstituted or substituted by at least one alkyl group (preferably a 2-tetrahydropyranyl group), and the other symbols are as hereinbefore defined.

The $OR^4$ group of compounds of general formula VIA may be converted to a hydroxy group by mild hydrolysis with an aqueous solution of an organic acid, e.g. acetic acid, or with a dilute aqueous inorganic acid, e.g. hydrochloric acid, advantageously in the presence of an organic solvent miscible with water, e.g. tetrahydrofuran or an alkanol containing from 1 to 4 carbon atoms, e.g. methanol. The mild hydrolysis may be carried out at a temperature ranging from ambient to 75° C. (preferably at a temperature below 45° C.) with an acid mixture, e.g. a mixture of hydrochloric acid with tetrahydrofuran or methanol, or a mixture of acetic acid, water and tetrahydrofuran.

The products of formula IVA may be purified by column chromatography on silica gel, which procedure may, when the starting material of formula VIA is a mixture of compounds with the group $OR^4$ in the 15-position in α- and β-configurations, lead to a separation of the resulting 15α- and 15β-hydroxy isomers of formula IVA.

Compounds of general formula VIA may be prepared from a compound of the general formula:

SH
⟨structure⟩ X COOR³
SH  Y  R¹
     OR⁴

(VIIA)

(wherein the various symbols are as hereinbefore defined) by oxidation with manganese dioxide in an inert organic solvent, e.g, toluene at a low temperature, e.g. −20° C., [cf. J. Org. Chem., 31, 1217 (1966)] or by air oxidation.

According to a further feature of the present invention, compounds of general formula IV wherein A represents a grouping of formula VB, in which the thiol groups attached to the 9- and 11-positions are in α-configuration, $R^2$ represents a hydrogen atom or a straight- or branched-chain alkyl group containing from 1 to 4 carbon atoms, and the other symbols are as hereinbefore defined, i.e. compounds of the general formula:

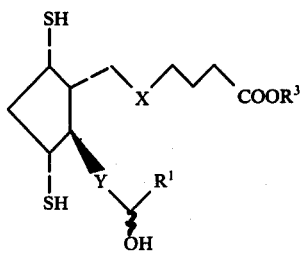

(IVB)

(wherein the various symbols are as hereinbefore defined) may be prepared from compounds of general formula VIIA wherein the various symbols are as hereinbefore defined by the application of the procedure hereinbefore described for the conversion of compounds of formula VIA into compounds of formula IVA.

According to a further feature of the present invention compounds of general formula IVA may also be prepared from corresponding compounds of general formula IVB (wherein the various symbols are as hereinbefore defined) by oxidation with manganese dioxide in an inert organic solvent, e.g. toluene at a low temperature, e.g. −20° C., [cf. J. Org. Chem., 31, 1217 (1966)] or by air oxidation.

Compounds of general formula VIIA may be prepared from a compound of the general formula:

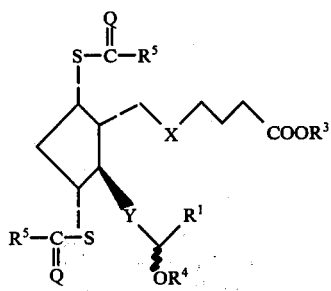

(VIIIA)

(wherein $R^5$ represents an alkyl group containing from 1 to 4 carbon atoms or a phenyl group, Q represents an oxygen or sulphur atom, $R^6$ represents an alkyl group containing from 1 to 4 carbon atoms and the other symbols are as hereinbefore defined) by hydrolysis under alkaline conditions.

The hydrolysis under alkaline conditions may be effected (1) with an aqueous solution of an alkali metal, e.g. sodium or potassium, hydroxide or carbonate in the presence of a water miscible solvent, e.g. tetrahydrofuran or an alkanol containing from 1 to 4 carbon atoms, to give a compound of general formula VIIA wherein $R^3$ represents a hydrogen atom, or (2) with anhydrous potassium carbonate in an anhydrous alkanol containing from 1 to 4 carbon atoms, preferably absolute methanol, to give a compound of general formula VIIA wherein $R^3$ represents an alkyl group containing from 1 to 4 carbon atoms.

Compounds of general formula VIIIA may be prepared from a compound of the general formula:

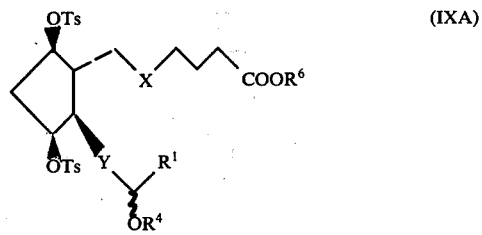

(IXA)

(wherein Ts represents a p-toluenesulphonyl or methanesulphonyl group and the other symbols are as hereinbefore defined) by reaction with a compound of the general formula:

(X)

$$R^5-\overset{O}{\underset{\|}{C}}-S-Na$$

(wherein the various symbols are as hereinbefore defined) in an inert organic solvent, for example a mixture of dimethyl sulphoxide and 1,2-dimethoxyethane at 0° to 50° C.

Compounds of general formula IXA may be prepared from a compound of the general formula:

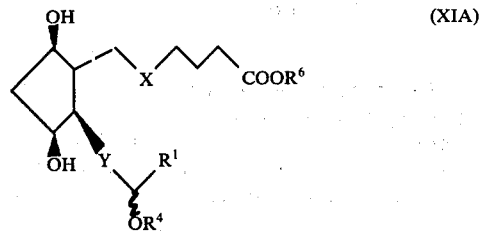

(XIA)

(wherein the various symbols are as hereinbefore defined) by reaction with p-toluenesulphonyl chloride or methanesulphonyl chloride in an inert organic solvent, e.g. methylene chloride in the presence of a base, for example pyridine or triethylamine, at a temperature ranging from 50° C. to −20° C.

The processes hereinbefore described may be represented by the series of reactions depicted schematically below in Scheme A wherein the various symbols are as hereinbefore defined.

SCHEME A

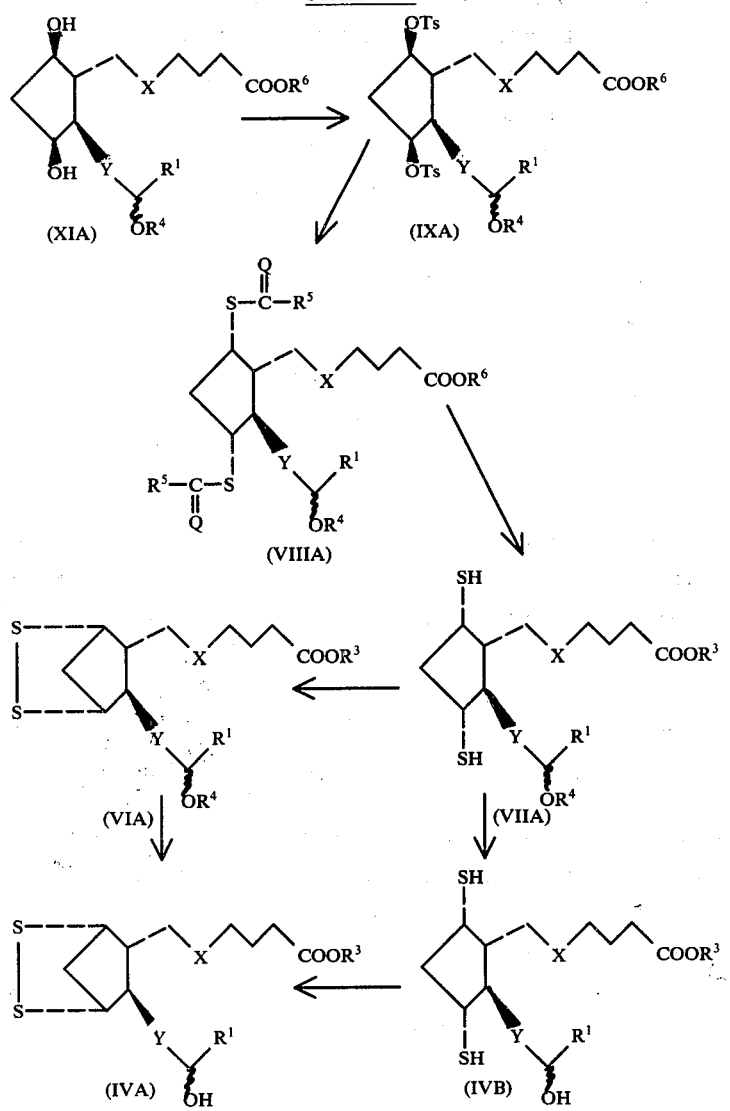

The compounds of general formula XIA, used as starting materials in the hereinbefore described procedure, may themselves be prepared from compounds of general formula XII below by the series of reactions depicted schematically in Scheme B, wherein Ac represents an acetyl group, $R^7$ represents a benzoyl or acetyl group, $R^8$ represents an alkylcarbonyl group containing from 2 to 5 carbon atoms, TMS represents a trimethylsilyl group and the other symbols are as hereinbefore defined.

SCHEME B

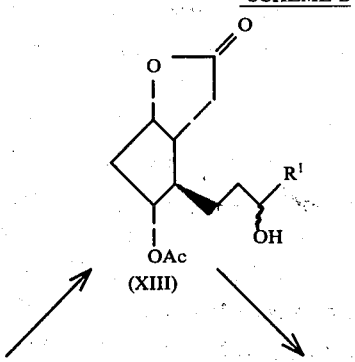

-continued
SCHEME B
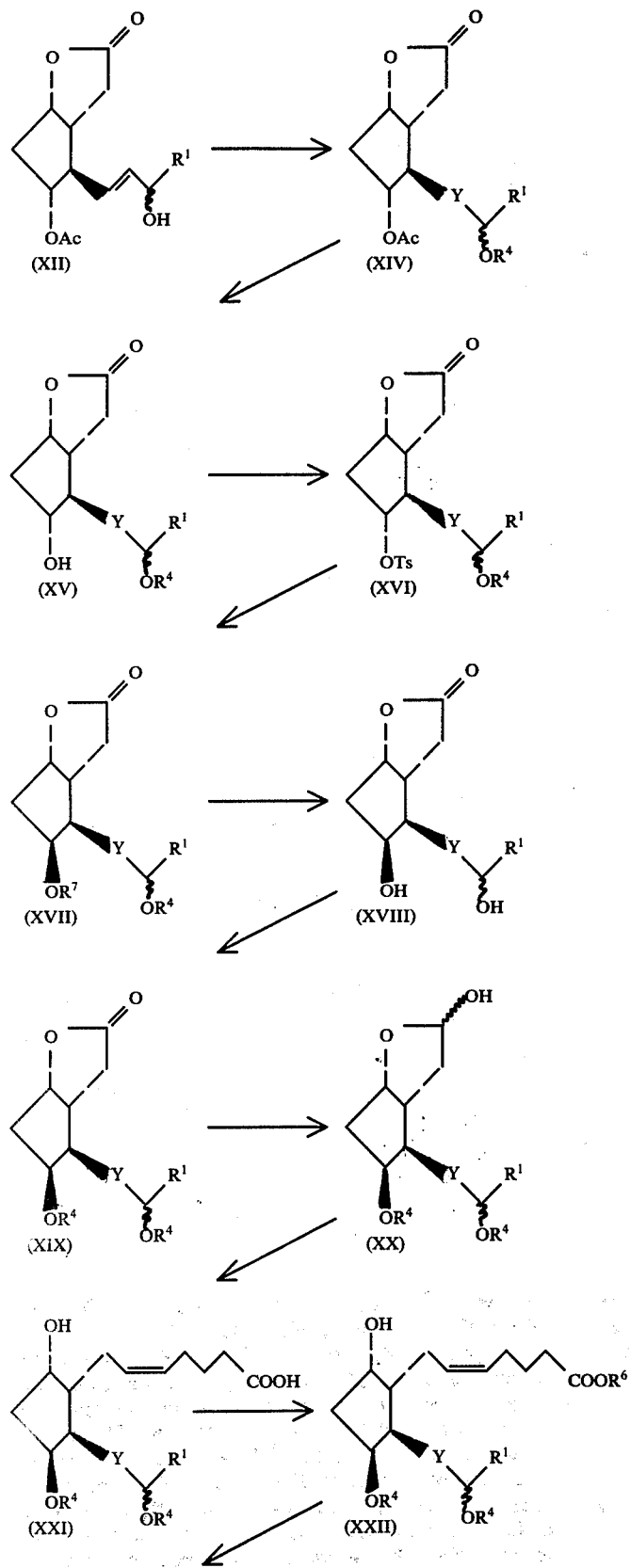

SCHEME B

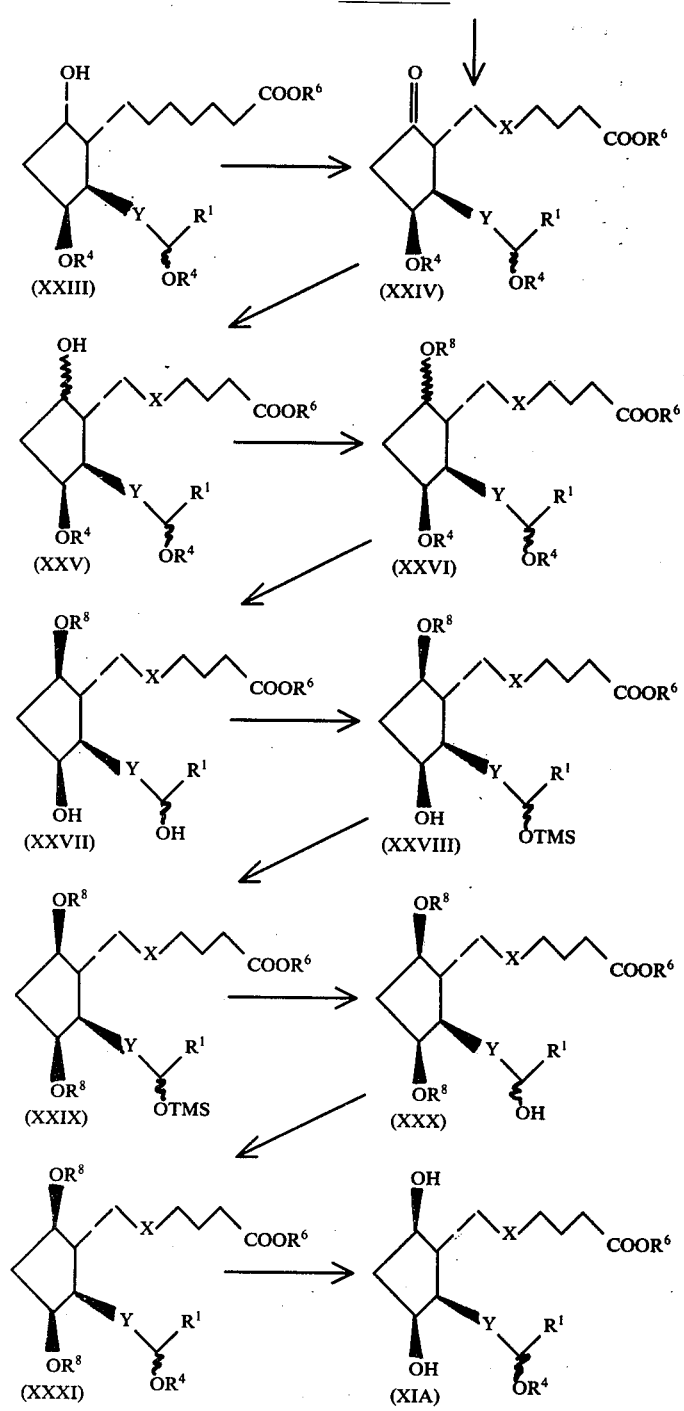

Compounds of formula XII may, if desired, be reduced to give compounds of formula XIII. Suitably, the reduction may be effected by hydrogenation in the presence of a hydrogenation catalyst, for example palladium on charcoal, palladium black or platinum dioxide, in the presence of an inert organic solvent, for example a lower alkanol, e.g. methanol or ethanol, at laboratory temperature at normal or elevated pressure, e.g. at a hydrogen pressure from atmospheric to 15 kilogrammes per square centimeter.

Compounds of formula XII or XIII are then reacted with a dihydropyran, dihydrofuran or ethyl vinyl ether in an inert solvent, e.g. methylene chloride, in the presence of a condensing agent, e.g. p-toluene-sulphonic acid to give compounds of formula XIV.

Compounds of formula XIV may be converted to compounds of formula XV by hydrolysis under alkaline conditions, for example with potassium carbonate in absolute methanol. Compounds of formula XV may be converted to compounds of formula XVI by means heretofore mentioned for the conversion of compounds of formula XIA to those of formula IXA. Compounds of formula XVI may be converted to compounds of formula XVII by reaction with sodium benzoate or tetraethylammonium acetate in N,N-dimethylformamide or dimethyl sulphoxide at 50° to 100° C. Compounds of formula XVII may be converted to compounds of formula XVIII by hydrolysis under alkaline conditions followed by hydrolysis under acidic conditions. The hydrolysis under alkaline conditions may be carried out by means heretofore mentioned for the conversion of compounds of formula VIIIA to those of formula VIIA, and the hydrolysis under acidic conditions may be carried out by means heretofore mentioned for the conversion of compounds of formula VIA to those of formula IVA. Compounds of formula XVIII may be converted to compounds of formula XIX by the application of the procedure hereinbefore described for the conversion of compounds of formula XII or XIII into compounds of formula XIV.

Compounds of formula XX may be prepared by reducing compounds of formula XIX with diisobutylaluminium hydride in toluene for about 30 minutes at −78° C.

Compounds of formula XXI may be prepared by reaction of a compound of formula XX with (4-carboxybutylidene)triphenylphosphorane obtained by the reaction of dimsyl anion, previously prepared from sodium hydride and dimethyl sulphoxide, with (4-carboxybutyl)triphenylphosphonium bromide. The (4-carboxybutylidene)triphenylphosphorane is reacted with a compound of formula XX in dimethyl sulphoxide for about one to five hours at a temperature ranging from ambient to 60° C. to yield a compound of formula XXI.

Compounds of formula XXI may be converted to compounds of formula XXII by esterification with (i) diazoalkane compounds, e.g. diazomethane, (ii) alcohols in the presence of dicyclohexylcarbodiimide as a condensing agent, (iii) alcohols following the formation of a mixed acid anhydride by adding a tertiary amine and then a pivaloyl halide or an arylsulphonyl or alkylsulphonyl halide (cf. our British Patent Specification Nos. 1362956 and 1364125), (iv) alkyl halides, e.g. methyl iodide, and (a) potassium carbonate in acetone [cf. J. Org. Chem., 34, 3717 (1969)], (b) sodium bicarbonate in N,N-dimethylacetamide or N,N-dimethylformamide [cf. Advan. Org. Chem., 5, 37 (1965)], (c) calcium oxide in dimethyl sulphoxide [cf. Synthesis, 262 (1972)], or (v) N,N-dimethylformamide-dialkylacetals, e.g. N,N-dimethylformamide-dimethylacetal, in dry benzene [cf. Helv. Chim. Acta, 48, 1746 (1965)].

Compounds of formula XXII may, if desired, be reduced to give compounds of formula XXIII by the application of the procedure hereinbefore described for the conversion of compounds of formula XII into compounds of formula XIII.

Compounds of formula XXII or XXIII may be converted to compounds of formula XXIV by methods known per se for the conversion of a hydroxy group in the 9-position of a prostaglandin compound to an oxo group, for example by means of a chromic acid solution (e.g. obtained from chromium trioxide, manganese sulphate, sulphuric acid and water) or Jones' reagent or dimethylsulphide-N-chlorosuccinimide complex [cf. J. Amer. Chem. Soc., 94, 7586 (1972)], or Collins' reagent. By the expression "methods known per se" as used in this specification is meant methods heretofore used or described in the literature.

Compounds of formula XXIV may be converted to compounds of formula XXV by reduction of the 9-oxo group to a hydroxy group. The reduction is suitably effected with excess sodium borohydride in an alkanol containing from 1 to 4 carbon atoms, e.g. methanol, at a low temperature, preferably at −30° to −60° C., or with zinc borohydride in a suitable inert organic solvent, e.g. 1,2-dimethoxyethane, at a temperature of −10° to 10° C. The product of formula XXV thus obtained is a mixture of isomers in which the hydroxy group at position 9 is in α- or β-configuration.

Compounds of formula XXV may be converted to compounds of formula XXVI by reaction with the appropriate acyl chloride or acid anhydride in an inert organic solvent, for example methylene chloride, in the presence of a base, for example pyridine or a tertiary amine, at a low temperature, e.g. at a temperature of 0° to 30° C.

Compounds of formula XXVI may be converted to compounds of formula XXVII by the application of the procedure hereinbefore described for the conversion of compounds of formula VIA into compounds of formula IVA, followed by separation of the compound of formula XXVII from its isomer having the group $OR^8$ in α-configuration by column chromatography of the mixture on silica gel. The proportion of β-configuration isomer to α-configuration isomer is about 10:1.

Compounds of formula XXVII may be converted to compounds of formula XXVIII by reaction with a suitable trimethylsilylating reagent, e.g. N-trimethylsilyldiethylamine or N,O-bis(trimethylsilyl)acetamide, in an inert organic solvent, e.g. acetone or methylene chloride, preferably at room temperature.

Compounds of formula XXVIII may be converted to compounds of formula XXIX by reaction with the appropriate acyl chloride or acid anhydride in an inert organic solvent, for example methylene chloride, in the presence of a base, for example pyridine or a tertiary amine, at a low temperature, e.g. at a temperature of 0° C. to 30° C. Compounds of formula XXX may be prepared by treating a compound of formula XXIX by methods known per se for the removal of the trimethylsilyl group, for example by treatment with an acid.

Compounds of formula XXX may be converted to compounds of formula XXXI by the application of the procedure hereinbefore described for the conversion of compounds of formula XII or XIII into compounds of formula XIV.

Compounds of formula XXXI may be converted to compounds of formula XIA by hydrolysis under alkaline conditions for example with potassium carbonate in absolute methanol.

The compounds of general formula XII may be prepared by the series of reactions depicted schematically below in Scheme C from the known compound of formula XXXII, i.e. 2-oxa-3-oxo-6-syn-formyl-7-anti-acetoxy-cis-bicyclo[3,3,0]octane, whose prepared is described in J. Amer. Chem. Soc., 92, 397 (1970) and ibid, 91, 5675 (1969):

SCHEME C

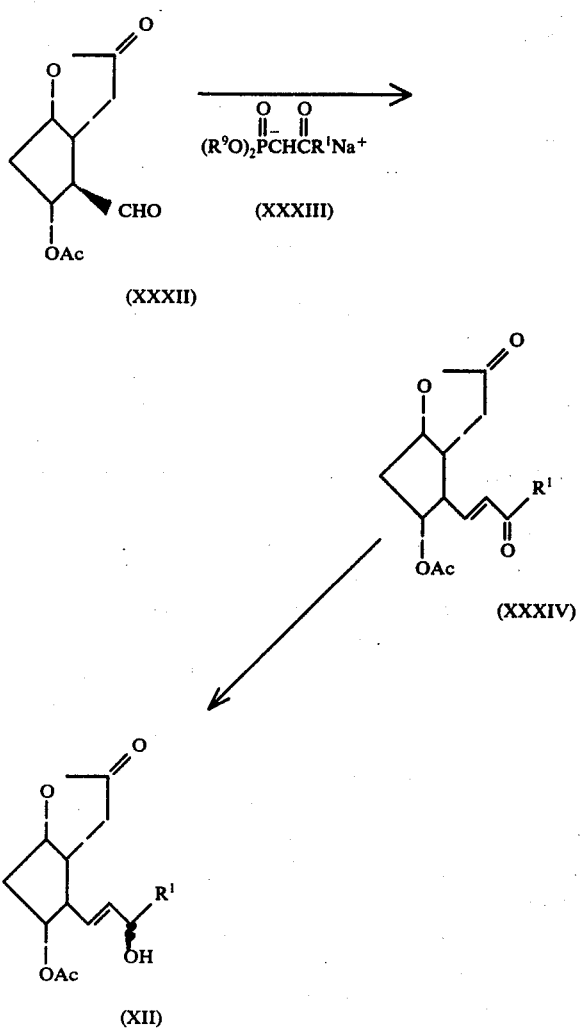

wherein $R^1$ and Ac are as hereinbefore defined and $R^9$ represents a methyl or ethyl group.

The bicyclo-octane aldehyde of formula XXXII is reacted with the sodio derivative of a dialkylphosphonate of formula XXXIII in an inert organic solvent, e.g. tetrahydrofuran or 1,2-dimethoxyethane, at 20° to 45° C. for about 1 to 2 hours, to form stereospecifically the trans-enone lactone of general formula XXXIV. The enone is treated with excess sodium borohydride in an inert solvent, for example a lower alkanol, e.g. methanol or ethanol, or tetrahydrofura, at a temperature of −45° C. to −30° C. for about 5 minutes, or with excess zinc borohydride in an inert solvent, e.g. 1,2-dimethoxyethane, at a temperature of −10° C. to 10° C., to reduce the carbonyl group in the side-chain to hydroxymethylene $$(\text{i.e.} -\underset{\underset{\text{OH}}{|}}{\text{CH}}-),$$

the treatment being carried out at a low temperature, e.g. 10° C. to −45° C., to prevent contemporaneous reduction of the conjugated carbon-carbon double bond, and to form a mixture (ratio about 1:1) of the α- and β-hydroxy epimers of the compound of general formula XII. If desired, separation of the α- and β-hydroxy epimers may be effected by column chromatography on silica gel using a mixture of diethyl ether-n-hexane-ethyl acetate (5:3:2) as eluent.

According to a further feature of the present invention, the prostaglandin analogues of general formula IV, wherein A represents a grouping of formula VA or VB and the bonds attaching the epidithio radical or the thiol radicals to the carbon atoms in the 9- and 11- positions are both in β-configuration, $R^2$ represents a hydrogen atom or a straight- or branched-chain alkyl group containing from 1 to 4 carbon atoms and the other symbols are as hereinbefore defined, i.e. compounds of the general formulae:

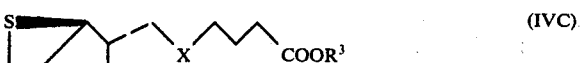

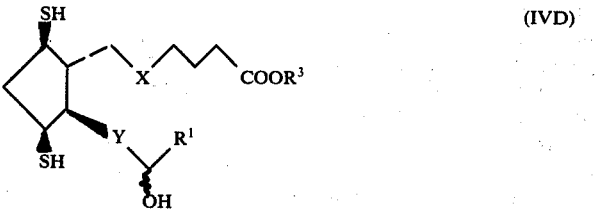

respectively, wherein the various symbols are as hereinbefore defined, may themselves be prepared from compounds of general formula XIB below by the series of reactions depicted schematically below in Scheme D (wherein the various symbols are as hereinbefore defined) by the application of the procedures hereinbefore described for the conversion of compounds of formula XIA into compounds of formulae IVA and IVB.

SCHEME D
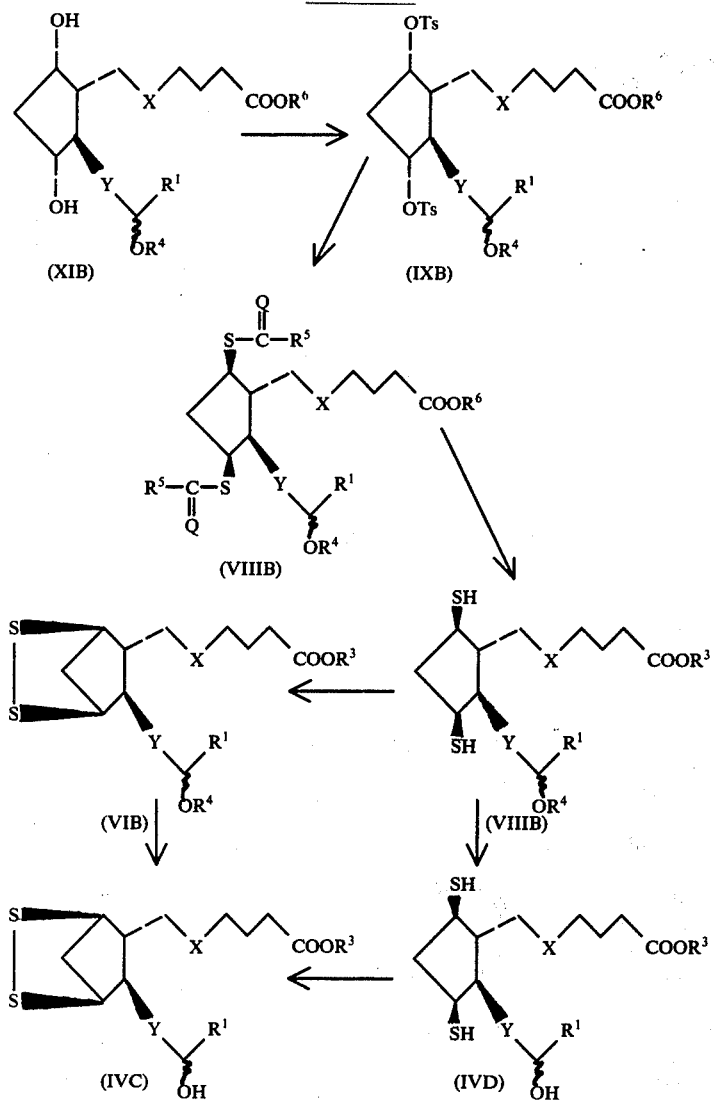
The compounds of general formula XIB, used as starting materials in the hereinbefore described procedure, may themselves be prepared from compounds of general formula XIV by the series of reactions depicted schematically below in Scheme E wherein the various symbols are as hereinbefore defined.
SCHEME E
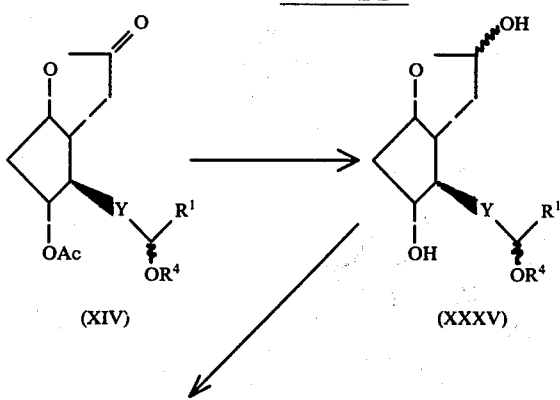

SCHEME E

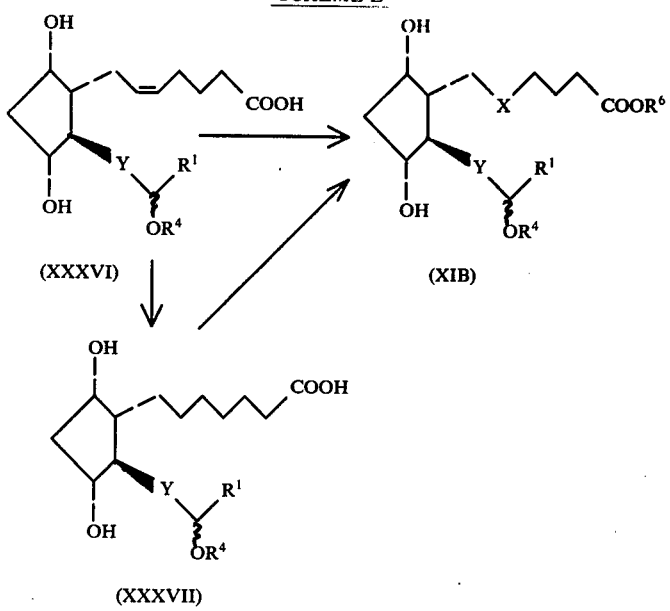

Compounds of formula XIV may be converted to compounds of formula XXXV by the application of the procedure hereinbefore described for the conversion of compounds of formula XIX into compounds of formula XX.

Compounds of formula XXXV may be converted to compounds of formula XXXVI by the application of the procedure hereinbefore described for the conversion of compounds of formula XX into compounds of formula XXI.

Compounds of formula XXXVI may, if desired, be reduced to give compounds of formula XXXVII by the application of the procedure hereinbefore described for the conversion of compounds of formula XII into compounds of formula XIII.

Compounds of formula XXXVI or XXXVII may be converted to compounds of formula XIB by means heretofore mentioned for the conversion of compounds of formula XXI to those of formula XXII.

Compounds of formula XVIII, hereinbefore depicted in Scheme B, may also be prepared from compounds of formula XXXVIII below by the series of reactions depicted schematically in Scheme F, wherein the various symbols are as hereinbefore defined.

SCHEME F

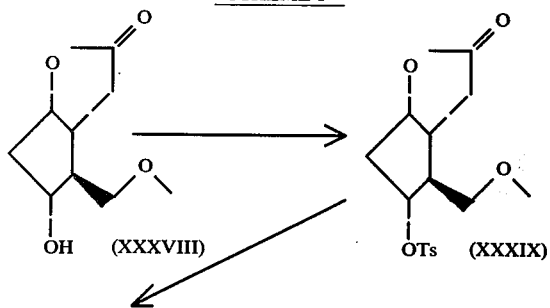

-continued SCHEME F

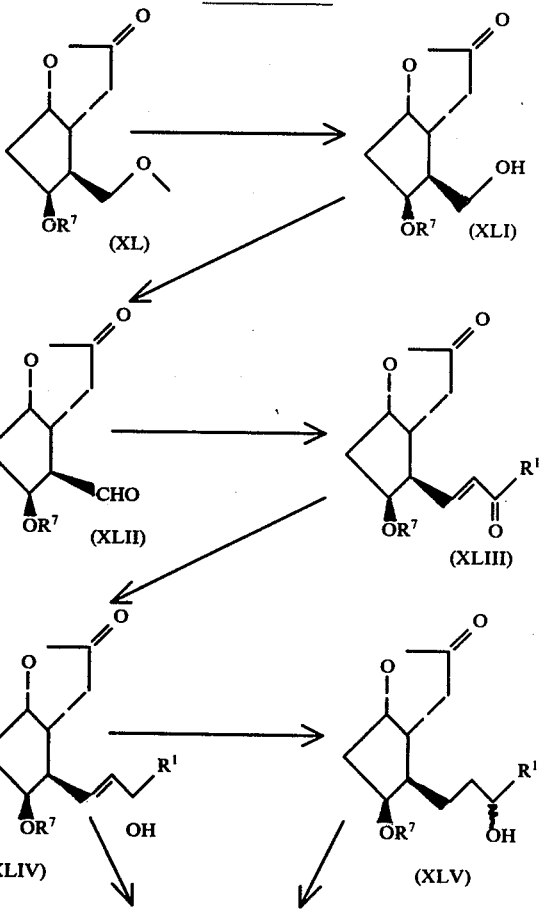

-continued
SCHEME F

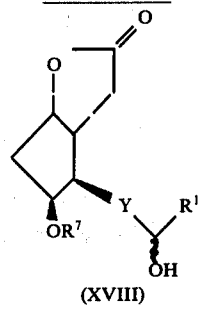

(XVIII)

The conversion of compounds of formula XXXVIII to those of formula XL (via compounds of formula XXXIX) may be carried out by means heretofore mentioned for the conversion of compounds of formula XV to those of formula XVII (via compounds of formula XVI).

Compounds of formula XLI may be prepared from compounds of formula XL by methods known per se [cf. J. Amer. Chem. Soc., 91, 5675 (1969)].

Compounds of formula XLI may be converted to compounds of formula XLII under mild and neutral conditions, for example with chromium trioxide-pyridine complex, Jones' reagent, dimethyl- or methylphenyl-sulphide-N-chlorosuccinimide complex, dimethyl- or methylphenylsulphide-chlorine complex [cf. J. Amer. Chem. Soc., 94, 7586 (1972)], or dicyclohexyl-carbodiimide-dimethyl sulphoxide complex [cf. J. Amer. Chem. Soc., 87, 5661 (1965)], at a moderately low temperature.

The conversion of compounds of formula XLII to those of formula XLIV (via compounds of formula XLIII) may be carried out by means heretofore mentioned for the conversion of compounds of formula XXXII to those of formula XII (via compounds of formula XXXIV).

Compounds of formula XLIV may be converted to compounds of formula XLV by means heretofore mentioned for the conversion of compounds of formula XII to those of formula XIII.

Compounds of formula XLIV or XLV may be converted to compounds of formula XVIII by hydrolysis under alkaline conditions.

According to a further feature of the present invention, the prostaglandin analogues of formula IV, wherein A represents a grouping of formula VB and the bonds attaching the thiol radicals to the carbon atoms in the 9- and 11-positions are in $\beta$- and $\alpha$-configuration, respectively, $R^2$ represents a hydrogen atom or a straight- or branched-chain alkyl group containing from 1 to 4 carbon atoms, and the other symbols are as hereinbefore defined, i.e. compounds of the general formula:

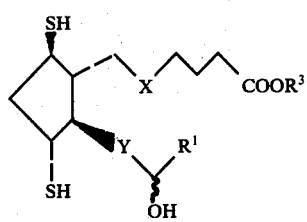

(IVE)

(wherein the various symbols are as hereinbefore defined) may be prepared from a compound of the general formula:

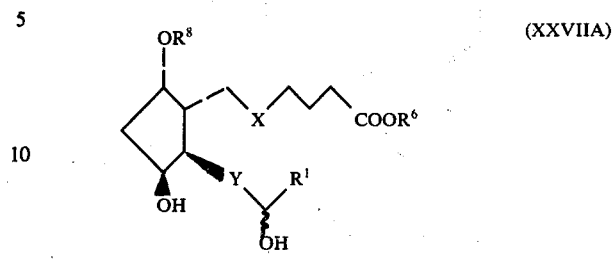

(XXVIIA)

(wherein the various symbols are as hereinbefore defined) by means heretofore mentioned for the conversion of compounds of formula XXVII to those of formula IVB (via compounds of formulae XIA and VIIA).

Compounds of formula XXVIIA may be separated from the mixture of compounds of formula XXVII and XXVIIA (prepared from compounds of formula XXVI as hereinbefore described) by column chromatography on silica gel.

According to a further feature of the present invention, the prostaglandin analogues of formula IV, wherein A represents a grouping of formula VB, and the bonds attaching the thiol radicals to the carbon atoms in the 9- and 11-positions are in $\alpha$- and $\beta$-configuration, respectively, $R^2$ represents a hydrogen atom, or a straight- or branched-chain alkyl group containing from 1 to 4 carbon atoms, and the other symbols are as hereinbefore defined, i.e. compounds of the general formula:

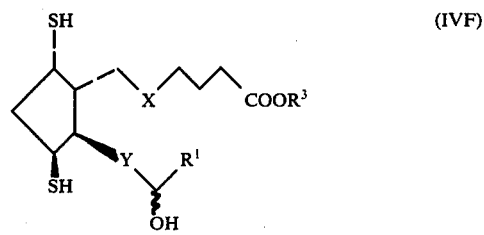

(IVF)

(wherein the various symbols are as hereinbefore defined) may be prepared from compounds of the general formula:

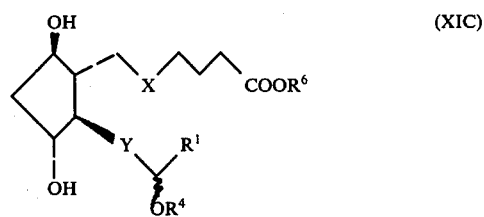

(XIC)

(wherein the various symbols are as hereinbefore defined) by means heretofore mentioned for the conversion of compounds of formula XIA to those of formula IVB (via compounds of general formula VIIA).

According to a feature of the invention, therefore, the prostaglandin analogues of formulae IVE and IVF, (wherein the various symbols are as hereinbefore defined) may be prepared from compounds of the general formulae:

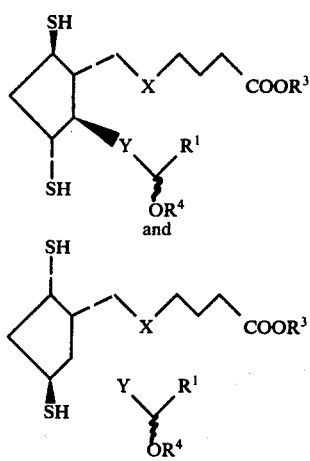

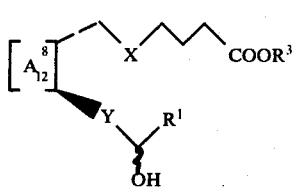

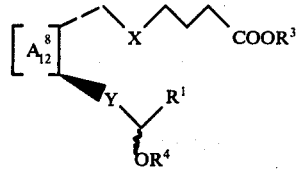

(wherein the various symbols are as hereinbefore defined), respectively, by the application of the procedures hereinbefore described for the conversion of compounds of formula VIA into prostaglandin analogues of formula IVA.

The present invention accordingly provides a process for the preparation of prostaglandin analogues of the general formula:

(wherein the various symbols are as hereinbefore defined) from compounds of the general formula:

(wherein the various symbols are as hereinbefore defined) by the application of the procedure hereinbefore described for the conversion of compounds of general formula VIA to prostaglandin analogues of formula IVA.

Compounds of formula XIC may be prepared from compounds of formula XIB by the series of reactions depicted schematically below in Scheme G, wherein the various symbols are as hereinbefore defined.

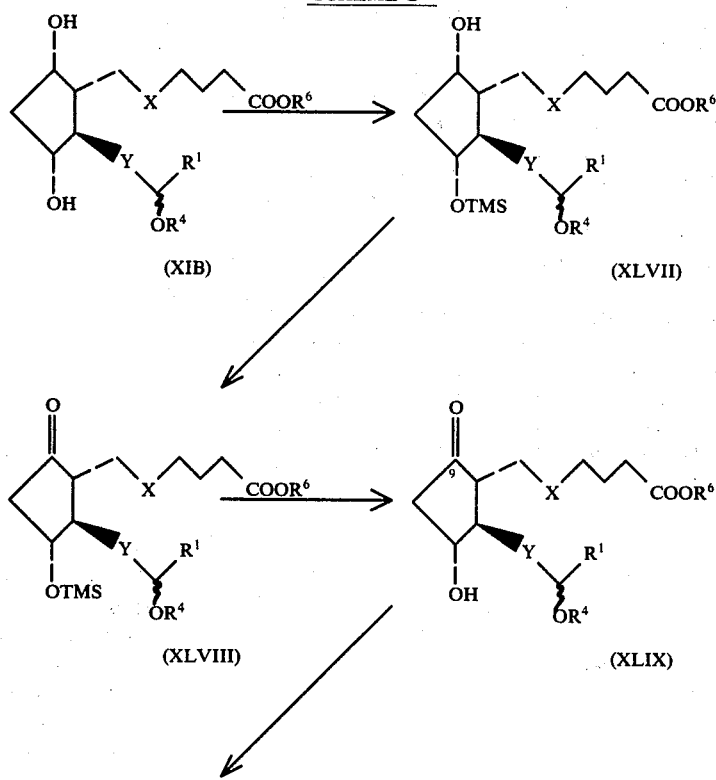

SCHEME G

SCHEME G

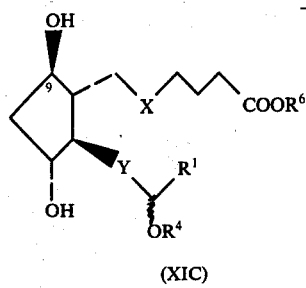

(XIC)

The conversion of compounds of formula XIB to those of formula XLVII may be carried out by means heretofore mentioned for the conversion of compounds of formula XXVII to those of formula XXVIII.

The conversion of compounds of formula XLVII to those of formula XLVIII may be carried out by means heretofore mentioned for the conversion of compounds of general formula XXIII to those of formula XXIV.

The conversion of compounds of formula XLVIII to those of formula XLIX may be carried out by means heretofore mentioned for the conversion of compounds of formula XXIX to those of formula XXX.

The conversion of compounds of formula XLIX to those of formula XIC may be carried out by means heretofore mentioned for the conversion of compounds of formula XXIV to those of formula XXV. The product thus obtained is a mixture of isomers in which the hydroxy group in the 9-position is in α- or β-configuration. The isomer having the hydroxy group in β-configuration may be separated from the isomer having the hydroxy group in α-configuration by column chromatography of the mixture on silica gel.

Esters of prostaglandin analogues of general formula IV, i.e. compounds of general formula IV wherein $R^2$ represents a straight- or branched-chain alkyl group containing from 1 to 12 carbon atoms and the various other symbols are as hereinbefore defined, may be obtained by reaction of the corresponding acids of general formula IV wherein $R^2$ represents a hydrogen atom with (i) the appropriate diazoalkane in a suitable inert solvent, e.g. diethyl ether, (ii) the appropriate alcohol in the presence of dicyclohexylcarbodiimide as condensing agent, or (iii) the appropriate alcohol following the formation of a mixed acid anhydride by adding a tertiary amine and then a pivaloyl halide or an arylsulphonyl or alkylsulphonyl halide (cf. our British Pat. Nos. 1362956 and 1364125).

The prostaglandin analogues of general formula IV wherein $R^2$ represents a hydrogen atom may, if desired, be converted by methods known per se into salts.

The salts may be prepared, for example, by reaction of stoichiometric quantities of an acid of general formula IV and the appropriate base, e.g. an alkali metal hydroxide or carbonate, ammonium hydroxide or carbonate, ammonia or an amine, in a suitable solvent. The salts may be isolated by lyophilisation of the solution or, if sufficiently insoluble in the reaction medium, by filtration, if necessary after removal of part of the solvent. Preferably the salts are non-toxic salts, i.e. salts the cations of which are relatively innocuous to the animal organism when used in therapeutic doses so that the beneficial pharmacological properties of the prostaglandins of general formula IV are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amine suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The prostaglandins of general formula IV may, if desired, be converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70° C. during the preparation of the cyclodextrin clathrates. α, β or γ-Cyclodextrins or mixtures thereof may be used in the preparation of the cyclodextrin clathrates. Conversion into their cyclodextrin clathrates serves to increase the stability of the prostaglandin compounds.

The prostaglandin analogues of general formula IV and their cyclodextrin clathrates and, when $R^2$ in general formula IV represents a hydrogen atom, their non-toxic salts, possess valuable and typical pharmacological properties. At low concentrations they produce blood vessel contraction and platelet aggregation and are expected to be useful as haemostatics in humans, large livestock such as cattle and horses and in pets, such as dogs and cats, where contraction of blood vessels and strong local platelet aggregation are desired and when the induced platelet aggregation is not harmful to the body. For example, in laboratory screening tests, (i) methyl 9α,11α-dimercapto-15α-hydroxyprosta-cis-5,trans-13-dienoate and methyl 9α,11α-epidithio-15α-hydroxyprosta-cis-5,trans-13-dienoate exhibited several times the platelet-aggregation-inducing activity of ADP (adenosinediphosphate) and (ii) methyl 9β,11β-epidithio-15α-hydroxyprosta-cis-5,trans-13-dienoate, methyl 9α,11α-epidithio-15α-hydroxyprosta-cis-5,trans-13-dienoate and methyl 9α,11α-dimercapto-15α-hydroxyprosta-cis-5,trans-13-dienoate exhibited, respectively, 500 times, 1,000 – 5,000 times and 5,000 times the rabbit aorta contractile activity of $PGE_1$.

The prostaglandin analogues of general formula IV, wherein A represents a grouping of formula VB, exhibit, at low concentrations, an inhibitory activity on the biosynthesis of prostaglandins from arachidonic acid and are useful as regulators of PG-biosynthesis in mammals, including humans when the control of PG-biosynthesis is desired. For example, in laboratory screening tests, the concentration of these compounds required to produce 50% inhibition of PG-biosynthesis was about 10 µM (PGF$_{2\alpha}$ used as a control produced no inhibition).

When the compounds of the present invention are to be used as haemostatics, when rapid cessation of bleeding is desired, for example during and after dental or oral surgery or after nasal surgery, the compounds are preferably applied, in a suitable carrier, to the site of bleeding. The carrier may optionally possess haemostatic activity.

For haemostatic use aqueous or non-aqueous solutions of the compounds of the invention may be used. Aqueous solutions may contain known additives to produce buffered or isotonic solutions and may also contain diluents, e.g. ethanol. Glycerol may be used as a non-aqueous solvent.

Other aqueous or non-aqueous preparations for haemostatic use include ointments, suppositories and aerosol preparations which may be used for local application and for the treatment of body cavities.

The compounds of the invention may also be used with other carriers which possess haemostatic activity, e.g. sponge and gauze containing absorbable gelatin.

Aqueous and non-aqueous solutions of the compounds of the invention for topical application preferably contain between 0.1 µg. and 100 µg. per ml. Haemostatic sponge or gauze for surgery preferably contains between 0.2 µg. and 500 µg. per gram.

The compounds of the invention may be used in various pharmaceutical compositions for haemostasis after surgical operations, e.g. dental, oral, nasal, gastric, duodenal, rectal, prostatic, gynaecological, nervous and other surgery and in the control of bleeding due to other causes such as trauma.

The prostaglandin analogues of general formula IV, wherein A represents a grouping of formula VB, may also be used to control prostaglandin biosynthesis for the alleviation of inflammation, pain and fever in mammals, particularly in humans. For this purpose the compounds of the invention are administered systemically, preferably orally, at a dosage from 0.001 µg. to 20 µg./kg. body weight. For the alleviation of severe symptoms the compounds may be administered by continuous intravenous infusion at a rate of 0.001 µg. to 20 µg./kg./min. until pain is alleviated.

For oral administration of prostaglandin analogues of general formula IV, wherein A represents a group of formula VB, the compounds, together with a pharmaceutical carrier or coating, may be administered as tablets, capsules or solutions. For intravenous administration sterilised isotonic solutions are preferred.

The present invention accordingly includes within its scope pharmaceutical compositions which comprise at least one therapeutically useful compound of general formula IV, or cyclodextrin clathrate thereof, or non-toxic salt thereof together with a pharmaceutical carrier or coating.

The following Reference Examples and Examples illustrate the preparation of new prostaglandin analogues of the present invention. In them NMR refers to nuclear magnetic resonance spectra, carried out in an approximately 10% w/v solution in deuterochloroform unless otherwise indicated, and the chemical shifts are expressed in parts per million; IR refers to infrared absorption spectra carried out on potassium bromide discs unless otherwise indicated; and TLC refers to thin layer chromatography on silica gel plates.

REFERENCE EXAMPLE 1

2-Oxa-3-oxo-6-syn-[3α-(2-tetrahydropyranyloxy)-oct-trans-1-enyl]-7-anti-acetoxy-cis-bicyclo[3,3,0]octane 27 g. of 2-oxa-3-oxo-6-syn-(3α-hydroxyoct-trans-1-enyl)-7-anti-acetoxy-cis-bicyclo[3,3,0]octane [prepared as described in J. Amer. Chem. Soc., 92, 397 (1970), and 91, 5675 (1969)] were dissolved in 250 ml. of dry methylene chloride. Whilst stirring at room temperature under an atmosphere of nitrogen, 15 ml. of 2,3-dihydropyran and 200 mg. of p-toluenesulphonic acid were added. After further stirring for 20 minutes, an aqueous solution of sodium bicarbonate was added and the reaction mixture was stirred for 5 minutes. Then, the reaction mixture was extracted with ethyl acetate; the extract was washed with water and an aqueous solution of sodium chloride, dried over sodium sulphate and concentrated under reduced pressure to give 34.3 g. of the title compound having the following physical characteristics:

TLC (developing solvent methylene chloride — methanol = 19:1): Rf = 0.69;

NMR (CDCl$_3$ solution): δ; 5.75–5.30 (2H, m), 5.30–4.76 (2H, m), 4.76–4.35 (1H, m), 2.03 (3H, s);

IR (liquid film): ν; 2940, 2860, 1770, 1735, 1435, 1365, 1235, 1125, 1035, 1020, 970, 900, 865, 815 cm$^{-1}$.

REFERENCE EXAMPLE 2

2-Oxa-3-hydroxy-6-syn-[3α-(2-tetrahydropyranyloxy)-oct-trans-1-enyl]-7-anti-hydroxy-cis-bicyclo[3,3,0]octane 34.3 g. of 2-oxa-3-oxo-6-syn-[3α-(2-tetrahydropyranyloxy)-oct-trans-1-enyl]-7-anti-acetoxy-cis-bicyclo[3,3,0]octane (prepared as described in Reference Example 1) were dissolved in 400 ml. of toluene. Whilst stirring and cooling to −78° C. under an atmosphere of nitrogen, 200 ml. of a 25% (w/v) solution of diisobutylaluminium hydride in toluene were added dropwise and the reaction mixture was stirred for 30 minutes. 10 ml. of methanol were then added, and the reaction mixture was warmed to 0° C. 100 ml. of water were then added, and the reaction mixture was stirred for 20 minutes. The precipitate was filtered off, and the filtrate was washed with an aqueous solution of sodium chloride, dried over sodium sulphate and concentrated under reduced pressure to give 30.8 g. of the title compound having the following physical characteristics:

TLC (developing solvent methylene chloride — methanol = 19:1): Rf = 0.33;

IR (liquid film): ν; 3400, 2940, 2860, 1435, 1350, 1110, 1075, 1020, 970 cm$^{-1}$;

NMR (CDCl$_3$ solution): δ; 5.90–5.00 (3H, m), 4.85–4.35 (1H, m).

REFERENCE EXAMPLE 3

9α,11α-Dihydroxy-15α-(2-tetrahydropyranyloxy)-prosta-cis-5,trans-13-dienoic acid To 200 ml. of a dimethyl sulphoxide solution of (4-carboxybutyl)triphenylphosphonium bromide (130 g.), dimsyl anion [obtained by heating 180 ml. of dimethyl sulphoxide containing 21 g. of sodium hydride (63% content) at 55° to 60° C. for 2 hours] was added dropwise at 23° to 27° C. After 5 minutes, 100 ml. of a dimethyl sulphoxide solution of 30.8 g. of 2-oxa-3-hydroxy-6-syn-[3α-(2-tetrahydropyranyloxy)-oct-trans-1-enyl]-7-anti-hydroxy-cis-bicyclo[3,3,0]octane (prepared as described in Reference Example 2) were added, and the solution was stirred for one hour. The reaction mixture was then added to 3–4 liters of ice-water containing a small amount of potassium carbonate and extracted with a mixture of diethyl ether and n-pentane (1:1) to eliminate by-products. The aqueous layer was then acidified with an aqueous solution of oxalic acid, and extracted with a mixture of diethyl ether and ethyl acetate (1:1). The organic layer was washed with water and an aqueous solution of sodium chloride, dried over sodium sulphate and concentrated under reduced pressure to give 38 g. of the title compound having the following physical characteristics:

TLC (developing solvent methylene chloride — methanol = 20:1): Rf = 0.21;

IR (liquid film): $\nu$; 3600–2400, 1710, 1460, 1440, 1380, 1250, 1200, 1195, 1120, 1110, 1080, 1060, 1040, 1020, 995 $cm^{-1}$.

REFERENCE EXAMPLE 4

Methyl
9α,11α-dihydroxy-15α-(2-tetrahydropyranyloxy)-prosta-cis-5,trans-13-dienoate To a solution of 38 g. of 9α,11α-dihydroxy-15α-(2-tetrahydropyranyloxy)-prosta-cis-5,trans-13-dienoic acid (prepared as described in Reference Example 3) in 200 ml. of diethyl ether, a freshly prepared ethereal solution of diazomethane was added at 0° to −20° C. until the reaction mixture showed a pale yellow colour. The reaction mixture was concentrated under reduced pressure and the residue was purified by column chromatography on silica gel using a mixture of benzene and ethyl acetate (3:2) as eluent to give 25 g. of the title compound having the following physical characteristics:

TLC (developing solvent benzene — ethyl acetate = 1:2): Rf = 0.34;

IR (liquid film): $\nu$; 3440, 2940, 2860, 1740, 1435, 1245, 1200, 1120, 1110, 1075, 1020, 980 $cm^{-1}$;

NMR (CDCl$_3$ solution): $\delta$; 5.75–5.22 (4H, m), 4.75–4.60 (1H, m), 4.60–3.25 (5H, m), 3.65 (3H, s).

REFERENCE EXAMPLE 5

Methyl
9α,11α-bis-(p-toluenesulphonyloxy)-15α-(2-tetrahydropyranyloxy)-prosta-cis-5,trans-13-dienoate To a solution of 25 g. of methyl 9α,11α-dihydroxy-15α-(2-tetrahydropyranyloxy)-prosta-cis-5,trans-13-dienoate (prepared as described in Reference Example 4) in 100 ml. of dry pyridine, there were added 42 g. of p-toluenesulphonyl chloride at 0° C. with stirring, and the mixture was stirred for 24 hours at room temperature. The reaction mixture was then poured into dilute hydrochloric acid at 0° C., extracted with ethyl acetate and the extract washed with water, an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (10:1) as eluent to give 14.85 g. of the title compound having the following physical characteristics:

TLC (developing solvent benzene — ethyl acetate = 4:1): Rf = 0.56;

IR (liquid film): $\nu$; 2940, 2870, 1740, 1600, 1440, 1320, 1245, 1190, 1180, 1100, 1040, 1025, 980, 905, 820 $cm^{-1}$;

NMR (CCl$_4$ solution): $\delta$; 7.90–7.02 (8H, m), 5.66–5.07 (4H, m), 5.07–4.69 (1H, m), 4.69–4.30 (2H, m), 3.61 (3H, s), 2.45 (6H, s).

REFERENCE EXAMPLE 6

Methyl
9β,11β-diacetylthio-15α-(2-tetrahydropyranyloxy)-prosta-cis-5,trans-13-dienoate To a suspension of 1.9 g. of sodium hydride (63% content) in 60 ml. of a mixture of dimethyl sulphoxide and 1,2-dimethoxyethane (2:1), there were added dropwise 3.7 ml. of thiolacetic acid at 0° C. with stirring under an atmosphere of nitrogen to give a sodium thiolacetate solution. To the reaction solution thus obtained, there was added a solution of 8.4 g. of methyl 9α,11α-bis-(p-toluenesulphonyloxy)-15α-(2-tetrahydropyranyloxy)-prosta-cis-5,trans-13-dienoate (prepared as described in Reference Example 5) in 30 ml. of a mixture of dimethyl sulphoxide and 1,2-dimethoxyethane (2:1) at 0° C., and the reaction mixture was stirred for 20 hours at room temperature. The reaction mixture was then poured into 500 ml. of ice-water, extracted with ethyl acetate, and the extract washed with an aqueous solution of sodium bicarbonate and an aqueous solution of sodium chloride, dried over sodium sulphate and concentrated under reduced pressure. The residue was subjected to column chromatography on silica gel, first using a mixture of benzene and ethyl acetate (20:1) as eluent to give 5 g. of the title compound contaminated with by-products, and then by column chromatography on silica gel using a mixture of cyclohexane and ethyl acetate (5:1) as eluent to give 2.35 g. of the title compound having the following physical characteristics:

TLC (developing solvent cyclohexane — ethyl acetate = 2:1): Rf = 0.55;

IR (liquid film): $\nu$; 2940, 2850, 1740, 1690, 1430, 1350, 1240, 1200, 1130, 1110, 1075, 1020, 980, 865 $cm^{-1}$;

NMR (CDCl$_3$ solution): $\delta$; 5.90–5.25 (4H, m), 4.88–4.60 (1H, m), 4.45–3.20 (4H, m), 3.65 (3H, s), 2.35 (6H, s).

EXAMPLE 1

Methyl
9β,11β-dimercapto-15α-(2-tetrahydropyranyloxy)-prosta-cis-5,trans-13-dienoate To a solution of 980 mg. of methyl 9β,11β-diacetylthio-15α-(2-tetrahydropyranyloxy)-prosta-cis-5,trans-13-dienoate (prepared as described in Reference Example 6) in 20 ml. of methanol, there were added 400 mg. of potassium carbonate at room temperature under an atmosphere of nitrogen. After stirring for 30 minutes, the reaction mixture was neutralized with acetic acid and diluted with ethyl acetate. The organic layer was washed with water, an aqueous solution of sodium bicarbonate and an aqueous solution of sodium chloride, dried over sodium sulphate and concentrated under reduced pressure. The residue was purified by column chromatography on silica gel using a mixture of cyclohexane and ethyl acetate (5:1) as eluent to give 659 mg. of the title compound having the following physical characteristics:

TLC (developing solvent cyclohexane — ethyl acetate = 2:1): Rf = 0.56 (tailing);

IR (liquid film): ν; 2940, 2860, 2550, 1740, 1435, 1370, 1310, 1245, 1160, 1130, 1115, 1080, 1025, 980 cm$^{-1}$;

NMR (CDCl$_3$ solution): δ; 5.80-5.10 (4H, m), 4.83-4.62 (1H, m), 4.29-3.10 (4H, m), 2.95-2.45 (1H, m), 1.80 (1H, d), 1.57 (1H, d).

EXAMPLE 2

Methyl 9β,11β-epidithio-15α-(2-tetrahydropyranyloxy)-prosta-cis-5,trans-13-dienoate 506 mg. of methyl 9β,11β-dimercapto-15α-(2-tetrahydropyranyloxy)-prosta-cis-5,trans-13-dienoate (prepared as described in Example 1) were dissolved in 30 ml. of toluene and the solution was stirred for 30 minutes under an atmosphere of nitrogen to exclude air. After cooling to −20° C., 1.5 g. of manganese dioxide was added and the mixture was stirred for 2 hours. The precipitate was then filtered off and washed with ethyl acetate. The filtrate was concentrated under reduced pressure. The residue was purified by column chromatography on silica gel using a mixture of benzene and ethyl acetate (20:1) as eluent to give 236 mg. of the title compound having the following physical characteristics:

TLC (developing solvent benzene — ethyl acetate = 6:1): Rf = 0.60;

IR (liquid film): ν; 2940, 2870, 1745, 1440, 1375, 1245, 1200, 1135, 1115, 1080, 1040, 1025, 985 cm$^{-1}$;

NMR (CDCl$_3$ soluton): δ; 5.94 (1H, dd), 5.70-5.00 (3H, m), 4.85-4.55 (1H, m), 3.67 (3H, s), 3.49-3.38 (1H, m), 2.82-2.60 (1H, m), 2.08-1.91 (2H, m).

EXAMPLE 3

Methyl 9β,11β-epidithio-15α-hydroxyprosta-cis-5,trans-13-dienoate

[(5Z,9β,11β,13E,15S)-9,11-Epidithio-15-hydroxy-prosta-5,13-dienoic acid methyl ester ]

764 mg. of methyl 9β,11β-epidithio-15α-(2-tetrahydropyranyloxy)-prosta-cis-5,trans-13-dienoate (prepared as described in Example 2) were dissolved in a mixture of 0.5 ml. of tetrahydrofuran and 5 ml. of a 65% acetic acid aqueous solution, and the mixture was stirred for 2 hours at 60° C. The reaction mixture was then diluted with 50 ml. of ethyl acetate, washed with water, an aqueous solution of sodium bicarbonate and an aqueous solution of sodium chloride, dried over sodium sulphate and concentrated under reduced pressure. The residue was purified by column chromatography on silica gel using a mixture of cyclohexane and ethyl acetate (6:1) as eluent to give 197 mg. of the title compound having the following physical characteristics:

TLC (developing solvent cyclohexane — ethyl acetate = 2:1): Rf = 0.33;

IR (liquid film): ν; 3430, 2930, 2860, 1740, 1430, 1365, 1250, 1170, 1020, 970 cm$^{-1}$;

NMR (CDCl$_3$ solution): δ; 5.99 (1H, dd), 5.50 (1H, dd), 5.70-5.25 (2H, m), 4.30-3.95 (1H, m), 3.68 (3H, s), 3.53-3.36 (1H, m), 2.85-2.56 (1H, m), 2.08-1.88 (2H, m).

REFERENCE EXAMPLE 7

2-Oxa-3-oxo-6-syn-[3α-(2-tetrahydropyranyloxy)-oct-trans-1-enyl]-7-anti-hydroxy-cis-bicyclo[3,3,0]octane To a solution of 12.7 g. of 2-oxa-3-oxo-6-syn-[3α-(2-tetrahydropyranyloxy)-oct-trans-1-enyl]-7-anti-acetoxy-cis-bicyclo[3,3,0]octane (prepared as described in Reference Example 1) in 100 ml. of methanol, there were added 5.5 g. of potassium carbonate, and the mixture was stirred for 20 minutes at room temperture. The reaction mixture was then neutralized with acetic acid, extracted with ethyl acetate, and the extract washed with water and an aqueous solution of sodium chloride, dried over sodium sulphate and concentrated under reduced pressure to give 11.4 g. of the title compound having the following physical characteristics:

TLC (developing solvent benzene — ethyl acetate = 1:2): Rf = 0.42;

IR (liquid film): ν; 3430, 2940, 2860, 1775, 1435, 1350, 1130, 1110, 1075, 1020, 975, 905 cm$^{-1}$;

NMR (CDCl$_3$ solution): δ; 5.75-5.24 (2H, m), 5.24-4.49 (2H, m), 3.38 (1H, s).

REFERENCE EXAMPLE 8

2-Oxa-3-oxo-6-syn-[3α-(2-tetrahydropyranyloxy)-oct-trans-1-enyl]-7-anti-(p-toluenesulphonyloxy)-cis-bicyclo[3,3,0]octane To a solution of 11.4 g. of 2-oxa-3-oxo-6-syn-[3α-(2-tetrahydropyranyloxy)-oct-trans-1-enyl]-7-anti-hydroxy-cis-bicyclo[3,3,0]octane (prepared as described in Reference Example 7) in 40 ml. of dry pyridine, there was added 20 g. of p-toluenesulphonyl chloride at 0° C. with stirring, and the mixture was stirred for 5 hours at room temperature. The reaction mixture was then poured into 300 ml. of ice-water, extracted with ethyl acetate, and the extract washed with an aqueous solution of oxalic acid, water, an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (5:1) as eluent to give 14.37 g. of the title compound as a crystalline solid having the following physical characteristics:

Melting point: 80° to 81° C.;

TLC (developing solvent benzene — ethyl acetate = 2:1): Rf = 0.55;

IR (CHCl$_3$ solution): ν; 3010, 2940, 2860, 1775, 1600, 1450, 1440, 1370, 1190, 1175, 1035, 1025, 975, 910 cm$^{-1}$;

NMR (CDCl$_3$ solution): δ; 8.10-7.15 (4H, m), 5.75-5.25 (2H, m), 5.15-4.40 (3H, m), 2.49 (3H, s).

REFERENCE EXAMPLE 9

2-Oxa-3-oxo-6-syn-[3α-(2-tetrahydropyranyloxy)-oct-trans-1-enyl]-7-syn-benzoyloxy-cis-bicyclo[3,3,0]octane To a solution of 14.3 g. of 2-oxa-3-oxo-6-syn-[3α-(2-tetrahydropyranyloxy)-oct-trans-1-enyl]-7-anti-(p-toluenesulphonyloxy)-cis-bicyclo[3,3,0]octane (prepared as described in Reference Example 8) in 500 ml. of N,N-dimethylformamide, there were added 40 g. of sodium benzoate, and the mixture was stirred for 4 hours at 90° to 100° C. under an atmosphere of nitrogen. The reaction mixture was then poured into 2 liters of water, extracted with ethyl acetate, and the extract washed with water and an aqueous solution of sodium chloride, dried over sodium sulphate and concentrated under reduced pressure. The residue was purified by column chromatography on silica gel using a mixture of benzene and ethyl acetate (5:1) as eluent to give 10.4 g. of the title compound having the following physical characteristics:

TLC (developing solvent benzene — ethyl acetate = 2:1): Rf = 0.68.

REFERENCE EXAMPLE 10

2-Oxa-3-oxo-6-syn-(3α-hydroxyoct-trans-1-enyl)-7-syn-hydroxy-cis-bicyclo[3,3,0]octane To a solution of 10.4 g. of 2-oxa-3-oxo-6-syn-[3α-(2-tetrahydropyranyloxy)-oct-trans-1-enyl]-7-syn-benzoyloxy-cis-bicyclo[3,3,0]octane (prepared as described in Reference Example 9) in 100 ml. of methanol, there were added 4 g. of potassium carbonate, and the mixture was stirred for one hour at 50° C. After cooling below room temperature, the reaction mixture was acidified with 2N hydrochloric acid and stirred for one hour. The reaction mixture was then poured into one liter of water, extracted with ethyl acetate, and the extract washed with an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (1:1) as eluent to give 1.94 g. of the title compound as a crystalline solid having the following physical characteristics:

Melting point: 75° C.;
TLC (developing solvent ethyl acetate): Rf = 0.36;
IR (CHCl$_3$ solution): $\nu$; 3400, 2930, 2855, 1770, 1415, 1375, 1245, 1165, 1095, 1035, 975, 905 cm$^{-1}$;
NMR (CDCl$_3$ solution): $\delta$; 5.95–5.60 (2H, m), 5.40–4.85 (1H, m), 4.55–3.85 (2H, m), 3.30 (2H, broad s).

REFERENCE EXAMPLE 11

2-Oxa-3-oxo-6-syn-[3α-(2-tetrahydropyranyloxy)-oct-trans-1-enyl]-7-syn-(2-tetrahydropyranyloxy)-cis-bicyclo[3,3,0]octane By proceeding as described in Reference Example 1, but using 1.94 g. of 2-oxa-3-oxo-6-syn-(3α-hydroxyoct-trans-1-enyl)-7-syn-hydroxy-cis-bicyclo[3,3,0]octane (prepared as described in Reference Example 10), 2.2 ml. of 2,3-dihydropyran and 20 mg. of p-toluenesulphonic acid, there were obtained 3.16 g. of the title compound having the following physical characteristics:

TLC (developing solvent ethyl acetate — benzene = 2:1); Rf = 0.68;
IR (liquid film): $\nu$; 2945, 2870, 1780, 1440, 1355, 1245, 1200, 1155, 1130, 1080, 1035, 1025, 985 cm$^{-1}$;
NMR (CDCl$_3$ solution): $\delta$; 6.00–5.32 (2H, m), 5.32–4.85 (1H, m), 4.85–4.50 (2H, m).

REFERENCE EXAMPLE 12

2-Oxa-3-hydroxy-6-syn-[3α-(2-tetrahydropyranyloxy)-oct-trans-1-enyl]-7-syn-(2-tetrahydropyranyloxy)-cis-bicyclo[3,3,0]octane By proceeding as described in Reference Example 2, but using 3.16 g. of 2-oxa-3-oxo-6-syn-[3α-(2-tetrahydroypyranyloxy)-oct-trans-1-enyl]-7-syn-(2-tetrahydropyranyloxy)-cis-bicyclo[3,3,0]octane (prepared as described in Reference Example 11) and 10 ml. of a 25% (w/v) solution of diisobutylaluminium hydride in toluene, there were obtained 3.17 g. of the title compound having the following physical characteristics:

TLC (developing solvent ethyl acetate — benzene = 2:1): Rf = 0.49;
IR (liquid film): $\nu$; 3400, 2950, 2870, 1435, 1345, 1260, 1198, 1130, 1110, 1075, 1020, 985 cm$^{-1}$;
NMR (CDCl$_3$ solution): $\delta$; 6.00–5.30 (2H, m), 5.15–4.48 (2H, m).

REFERENCE EXAMPLE 13

Methyl 9α-hydroxy-11β,15α-bis-(2-tetrahydropyranyloxy)-prosta-cis-5,trans-13-dienoate By proceeding as described in Reference Example 3, but using 3.17 g. of 2-oxa-3-hydroxy-6-syn-[3α-(2-tetrahydropyranyloxy)-oct-trans-1-enyl]-7-syn-(2-tetrahydropyranyloxy)-cis-bicyclo[3,3,0]octane (prepared as described in Reference Example 12); there was obtained 9α-hydroxy-11β,15α-bis-(2-tetrahydropyranyloxy)-prosta-cis-5,trans-13-dienoic acid, which was used as starting material in the procedure described in Reference Example 4 to yield the title compound as a crude product. The crude product was purified by column chromatography on silica gel using a mixture of benzene and ethyl acetate (3:1) as eluent to give 2.74 g. of the title compound having the following physical characteristics:

TLC (developing solvent ethyl acetate — benzene = 2:1): Rf = 0.53;
IR (liquid film): $\nu$; 3460, 2940, 2860, 1740, 1435, 1355, 1320, 1200, 1135, 1115, 1075, 1020, 985 cm$^{-1}$;
NMR (CDCl$_3$ solution): $\delta$; 6.00–5.20 (4H, m), 4.90–4.55 (2H, m), 3.65 (3H, s).

REFERENCE EXAMPLE 14

Methyl 9-oxo-11β,15α-bis-(2-tetrahydropyranyloxy)-prosta-cis-5,trans-13-dienoate 5 g. of chromium trioxide, 28 g. of manganese sulphate and 6 ml. of sulphuric acid were dissolved in 120 ml. of water to give a chromic acid solution. The solution thus obtained was cooled to 0° C. and added to a solution of 2.7 g. of methyl 9α-hydroxy-11β,15α-bis-(2-tetrahydropyranyloxy)-prosta-cis-5,trans-13-dienoate (prepared as described in Reference Example 13) in 120 ml. of diethyl ether at 0° C. After stirring for one hour at 0° to 5° C., the reaction mixture was extracted with diethyl ether, and the extract washed with water and an aqueous solution of sodium chloride, dried over sodium sulphate and concentrated under reduced pressure. The residue was purified by column chromatography on silica gel using a mixture of benzene and ethyl acetate (4:1) as eluent to give 2.54 g. of the title compound having the following physical characteristics:

TLC:
(i) developing solvent (benzene — ethyl acetate = 2:1) development (×1) Rf = 0.58, 0.53 (2 spots: diastereomers, centre of chirality at the 2-position of the tetrahydropyranyl ring);
(ii) developing solvent (benzene — ethyl acetate = 3:1) development (×2) Rf = 0.38, 0.37, 0.29, 0.27 (4 spots: diastereomers, centre of chirality at the 2-position of the tetrahydropyranyl ring);
IR (liquid film): $\nu$; 2940, 2870, 1740, 1435, 1380, 1320, 1200, 1160, 1130, 1110, 1075, 1035, 1020, 980 cm$^{-1}$;
NMR (CDCl$_3$ solution): $\delta$; 6.10–5.10 (4H, m), 5.00–4.60 (2H, m), 4.60–3.15 (6H, m), 3.68 (3H, s).

REFERENCE EXAMPLE 15

Methyl 9ξ-hydroxy-11β,15α-bis-(2-tetrahydropyranyloxy)-prosta-cis-5,trans-13-dienoate To a solution of 2.53 g. of methyl 9-oxo-11β,15α-bis-(2-tetrahydropyranyloxy)-prosta-cis-5,trans-13-dienoate (prepared as described in Reference Example 14) in 30 ml. of methanol, there was added 0.8 g. of sodium borohydride slowly at $-50°$ C. with stirring. After stirring for 30 minutes at $-50°$ C., the reaction mixture was quenched with acetic acid and concentrated under reduced pressure. The residue was diluted with ethyl acetate, washed with water, an aqueous solution of sodium bicarbonate and an aqueous solution of sodium chloride, dried over sodium sulphate and concentrated under reduced pressure to give 2.54 g. of the title compound having the following physical characteristics:

TLC: developing solvent (benzene -ethyl acetate = 3:1) development ($\times 2$) Rf = 0.39, 0.37, 0.34 (3 spots);

IR (liquid film): ν; 3450, 2940, 2860, 1740, 1435, 1350, 1320, 1240, 1200, 1130, 1115, 1080, 1020, 985 cm$^{-1}$;

NMR (CDCl$_3$ solution): δ; 6.00–5.05 (4H, m), 5.05–4.50 (2H, m), 4.50–3.10 (7H, m), 3.68 (3H, s).

REFERENCE EXAMPLE 16

Methyl 9ξ-acetoxy-11β,15α-bis-(2-tetrahydropyranyloxy)-prosta-cis-5,trans-13-dienoate To a solution of 2.54 g. of methyl 9ξ-hydroxy-11β,15α-bis-(2-tetrahydropyranyloxy)-prosta-cis-5,trans-13-dienoate (prepared as described in Reference Example 15) in 30 ml. of dry pyridine, there were added 2.5 ml. of acetic anhydride, and the mixture was stirred overnight at room temperature under an atmosphere of nitrogen. The reaction mixture was then poured into 200 ml. of ice-water, extracted with ethyl acetate, and the extract washed with an aqueous solution of oxalic acid, an aqueous solution of sodium bicarbonate and an aqueous solution of sodium chloride, dried over sodium sulphate and concentrated under reduced pressure to give 2.74 g. of the title compound having the following physical characteristics:

TLC (developing solvent benzene — ethyl acetate = 2:1): Rf = 0.60;

IR (liquid film): ν; 2950, 2870, 1740, 1440, 1370, 1250, 1200, 1135, 1115, 1080, 1040, 1025, 985 cm$^{-1}$;

NMR (CDCl$_3$ solution): δ; 6.00–5.20 (4H, m), 5.12–4.55 (3H, m), 3.68 (3H, s), 2.05 (3H, s).

REFERENCE EXAMPLE 17

Methyl 9β-acetoxy-11β,15α-dihydroxy-prosta-cis-5,-trans-13-dienoate 2.73 g. of methyl 9ξ-acetoxy-11β,15α-bis-(2-tetrahydropyranyloxy)-prosta-cis-5,trans-13-dienoate (prepared as described in Reference Example 16) was dissolved in a mixture of 3 ml. of tetrahydrofuran and 30 ml. of 65% aqueous acetic acid, and the mixture was stirred for 30 minutes at 60° to 70° C. The reaction mixture was then diluted with 200 ml. of ethyl acetate, washed with water, an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (2:1) as eluent to give 1.62 g. of the title compound and 160 mg. of its 9α-acetoxy isomer. The title compound showed the following physical characteristics:

TLC (developing solvent benzene — ethyl acetate = 1:2): Rf = 0.22; (9α-acetoxy isomer: Rf = 0.30);

IR (liquid film): ν; 3430, 2940, 2860, 1740, 1435, 1365, 1250, 1090, 1030, 980 cm$^{-1}$;

NMR (CDCl$_3$ solution): δ; 5.95–5.65 (2H, m), 5.65–5.30 (2H, m), 5.20–4.70 (1H, m), 4.60–3.90 (2H, m), 3.68 (3H, s), 3.18 (2H, broad s), 2.05 (3H, s).

REFERENCE EXAMPLE 18

Methyl 9β,11β-diacetoxy-15α-hydroxy-prosta-cis-5,trans-13-dienoate

To a solution of 1.61 g. of methyl 9β-acetoxy-11β,15α-dihydroxy-prosta-cis-5,trans-13-dienoate (prepared as described in Reference Example 17) in 10 ml. of dry acetone, there were added 3.5 ml. of N-trimethyl silyldiethylamine at room temperature with stirring under an atmosphere of nitrogen. After stirring for 3 hours (following the course of the reaction by TLC), an aqueous solution of sodium bicarbonate was added and the reaction mixture was extracted with ethyl acetate. The organic layer was washed with an aqueous solution of sodium chloride, dried over sodium sulphate and concentrated under reduced pressure to give methyl 9β-acetoxy-11β-hydroxy-15α-trimethylsilyloxy-prosta-cis-5,trans-13-dienoate. A sample of the product thus obtained showed the following physical characteristic:

TLC (developing solvent cyclohexane — ethyl acetate = 2:1): Rf = 0.37;

This compound was again dissolved in a mixture of 30 ml. of dry methylene chloride and 3 ml. of dry pyridine. To the solution obtained, there was added 5.5 ml. of acetyl chloride solution in methylene chloride (prepared by dissolving 0.57 ml. of acetyl chloride in 10 ml. of dry methylene chloride) at $-70°$ C. with stirring under an atmosphere of nitrogen. After slowly warming to room temperature, the reaction mixture was stirred for 30 minutes. The reaction mixture was then poured into dilute hydrochloric acid at 0° C.; extracted with ethyl acetate and the extract was concentrated under reduced pressure to give methyl 9β,11β-diacetoxy-15α-trimethylsilyloxy-prosta-cis-5,trans-13-dienoate. A sample of the product thus obtained showed the following physical characteristic:

TLC (developing solvent cyclohexane — ethyl acetate = 2:1): Rf = 0.50;

This compound was again dissolved in 30 ml. of ethyl acetate. To the solution obtained, there was added 30 ml. of 1N hydrochloric acid and 5 ml. of methanol and the mixture was stirred for 30 minutes at room temperature. The reaction mixture was extracted with ethyl acetate and the extract washed with water, an aqueous solution of sodium bicarbonate and an aqueous solution of sodium chloride, dried over sodium sulphate and concentrated under reduced pressure. The residue was purified by column chromatography on silica gel using a mixture of cyclohexane and ethyl acetate (3:1) as eluent to give 1.49 g. of the title compound and 216 mg. of the starting material. The title compound showed the following physical characteristics:

TLC (developing solvent cyclohexane — ethyl acetate = 2:1): Rf = 0.13;

IR (liquid film): ν; 3500, 2940, 2860, 1740, 1435, 1375, 1250, 1015, 975 cm$^{-1}$;

NMR (CDCl$_3$ solution): δ; 5.95–5.34 (4H, m), 5.34–4.60 (2H, m), 4.55–3.93 (1H, m), 3.68 (3H, s), 2.05 (6H, s).

REFERENCE EXAMPLE 19

Methyl 9β,11β-diacetoxy-15α-(2-tetrahydropyranyloxy)-prosta-cis-5,trans-13-dienoate By proceeding as described in Reference Example 1, but using 1.04 g. of methyl 9β,11β-diacetoxy-15α-hydroxyprosta-cis-5,trans-13-dienoate (prepared as described in Reference Example 18) there was obtained 1.23 g. of the title compound having the following physical characteristics:

TLC (developing solvent benzene — ethyl acetate = 2:1): Rf = 0.73;

IR (liquid film): ν; 2940, 2850, 1730, 1430, 1370, 1220, 1075, 1030, 1020, 975 cm$^{-1}$;

NMR (CDCl$_3$ solution): δ; 5.95–5.33 (4H, m), 5.33–4.50 (3H, m), 4.50–3.20 (3H, m), 3.68 (3H, s), 2.05 (6H, s).

REFERENCE EXAMPLE 20

Methyl 9β,11β-dihydroxy-15α-(2-tetrahydropyranyloxy)-prosta-cis-5,trans-13-dienoate To a solution of 1.23 g. of methyl 9β,11β-diacetoxy-15α-(2-tetrahydropyranyloxy)-prosta-cis-5,trans-13-dienoate (prepared as described in Reference Example 19) in 20 ml. of methanol, there was added 700 mg. of potassium carbonate and the mixture was stirred for one hour at 45° C. The reaction mixture was then neutralized with acetic acid and diluted with 200 ml. of ethyl acetate. The organic layer was washed with water, an aqueous solution of sodium bicarbonate and an aqueous solution of sodium chloride, dried over sodium sulphate and concentrated under reduced pressure to give 1.04 g. of the title compound having the following physical characteristics:

TLC (developing solvent benzene — ethyl acetate = 2:1): Rf = 0.10;

IR (liquid film): ν; 3430, 2940, 2860, 1740, 1440, 1320, 1200, 1155, 1130, 1115, 1025, 985 cm$^{-1}$;

NMR (CDCl$_3$ solution): δ; 5.95–5.30 (4H, m), 5.10–4.60 (1H, m), 4.50–3.40 (5H, m), 3.68 (3H, s), 3.22 (2H, broad s).

REFERENCE EXAMPLE 21

Methyl 9β,11β-bis-(p-toluenesulphonyloxy)-15α-(2-tetrahydropyranyloxy)-prosta-cis-5,trans-13-dienoate To a solution of 1.04 g. of methyl 9β,11β-dihydroxy-15α-(2-tetrahydropyranyloxy)-prosta-cis-5,trans-13-dioenoate (prepared as described in Reference Example 20) in 20 ml. of dry pyridine, there were added 2 g. of p-toluenesulphonyl chloride. After stirring overnight at room temperature, the reaction mixture was stirred for a further 3 hours at 70° C. The reaction mixture was then poured into ice-water, extracted with ethyl acetate, and the extract washed with dilute hydrochloric acid, an aqueous solution of sodium bicarbonate and an aqueous solution of sodium chloride, dried over sodium sulphate and concentrated under reduced pressure. The residue was purified by column chromatography on silica gel using a mixture of benzene and ethyl acetate (20:1 to 10:1) as eluent to give 611 mg. of the title compound and 253 mg. of methyl 9β-(p-toluenesulphonyloxy)-11β-hydroxy-15α-(2-tetrahydropyranyloxy)-prosta-cis-5,trans-13-dienoate. The title compound showed the following physical characteristics:

TLC (developing solvent benzene — ethyl acetate = 4:1): Rf = 0.58, 0.51 (2 spots: diastereomers, centre of chirality at the 2-position of the tetrahydropyranyl ring);

IR (liquid film): ν; 2950, 2880, 1740, 1600, 1440, 1370, 1250, 1195, 1180, 1105, 1080, 1025, 980, 905, 820 cm$^{-1}$;

NMR (CDCl$_3$ solution): δ; 8.10–7.65 (4H, m), 7.65–7.20 (4H, m), 5.85–5.05 (4H, m), 5.05–4.40 (3H, m), 4.40–3.20 (3H, m), 3.70 (3H, s), 2.48 (6H, s).

REFERENCE EXAMPLE 22

Methyl 9α,11α-diacetylthio-15α-(2-tetrahydropyranyloxy)-prosta-cis-5,trans-13-dienoate By proceeding as described in Reference Example 6, but using 610 mg. of methyl 9β,11β-bis-(p-toluenesulphonyloxy)-15α-(2-tetrahydropyranyloxy)-prosta-cis-5,trans-13-dienoate (prepared as described in Reference Example 21) there was obtained the title compound as a crude product. The crude product was subjected to column chromatography on silica gel, first using a mixture of benzene and ethyl acetate (20:1) as eluent to give the title compound contaminated with by-products, and then using a mixture of cyclohexane and ethyl acetate (6:1) as eluent to give 310 mg. of the title compound having the following physical characteristics:

TLC:

(i) developing solvent (benzene — ethyl acetate = 6:1): Rf = 0.56;

(ii) developing solvent (cyclohexane — ethyl acetate = 2:1): Rf = 0.54;

IR (liquid film): ν; 2950, 2870, 1740, 1695, 1435, 1350, 1240, 1200, 1130, 1115, 1080, 1025, 980 cm$^{-1}$;

NMR (CDCl$_3$ solution): δ; 5.70–5.10 (4H, m), 4.78–4.46 (1H, m), 4.24–3.20 (4H, m), 3.66 (3H, s), 3.10–2.65 (1H, m), 2.32 (3H, s), 2.28 (3H, s).

EXAMPLE 4

Methyl 9α,11α-dimercapto-15α-(2-tetrahydropyranyloxy)-prosta-cis-5,trans-13-dienoate By proceeding as described in Example 1, but using 400 mg. of methyl 9α,11α-diacetylthio-15α-(2-tetrahydropyranyloxy)-prosta-cis-5,trans-13-dienoate (prepared as described in Reference Example 22) there was obtained the title compound as a crude product. The crude product was purified by column chromatography on silica gel using a mixture of cyclohexane and ethyl acetate (6:1) as eluent to give 343 mg. of the title compound having the following physical characteristics:

TLC (developing solvent cyclohexane — ethyl acetate = 2:1: Rf = 0.58 (tailing);

IR (liquid film): ν; 2950, 2860, 2560, 1740, 1435, 1315, 1200, 1135, 1115, 1080, 1040, 1025, 985 cm$^{-1}$;

NMR (CDCl$_3$ solution): δ; 5.90–5.10 (4H, m), 4.85–4.60 (1H, m), 4.23–3.26 (4H, m), 3.66 (3H, s), 3.10–2.60 (1H, m), 1.76 (1H, d), 1.56 (1H, d).

EXAMPLE 5

Methyl 9α,11α-epidithio-15α-(2-tetrahydropyranyloxy)-prosta-cis-5,trans-13-dienoate By proceeding as described in Example 2, but using 243 mg. of methyl 9α,11α-dimercapto-15α-(2-tetrahydropyranyloxy)-prosta-cis-5,trans-13-dienoate (prepared as described in Example 4) there was obtained the title compound as a crude product. The crude product was purified by column chromatography on silica gel using a mixture of benzene and ethyl acetate (6:1) as eluent to give 87 mg. of the title compound having the following physical characteristics:

TLC (developing solvent cyclohexane — ethyl acetate = 2:1): Rf = 0.55;

IR (liquid film): ν; 2950, 2870, 1735, 1435, 1370, 1245, 1200, 1130, 1115, 1075, 1020, 980 cm$^{-1}$;

NMR (CDCl$_3$ solution): δ; 5.73–5.05 (4H, m), 4.92–4.46 (1H, m), 4.25–3.18 (4H, m), 3.67 (3H, s), 3.18–2.68 (1H, m).

EXAMPLE 6

Methyl 9α,11α-epidithio-15α-hydroxyprosta-cis-5,trans-13-dienoate

[(5Z,9α,11α,13E,15S)-9,11-Epidithio-15-hydroxy-prosta-5,13-dienoic acid methyl ester]

By proceeding as described in Example 3, but using 87 mg. of methyl 9α,11α-epidithio-15α-(2-tetrahydropyranyloxy)-prosta-cis-5,trans-13-dienoate (prepared as described in Example 5) there were obtained 23 mg. of the title compound having the following physical characteristics:

TLC:
(i) developing solvent (cyclohexane — ethyl acetate = 2:1): Rf = 0.43;
(ii) developing solvent (chloroform — ethanol = 50:1): Rf = 0.20;

IR (liquid film): ν; 3450, 2940, 2860, 1740, 1435, 1365, 1260, 1195, 1175, 1020, 975 cm$^{-1}$;

NMR (CDCl$_3$ solution): δ; 5.90–5.10 (4H, m), 4.30–3.90 (1H, m), 3.90–3.20 (2H, m), 3.67 (3H, s), 3.20–2.68 (2H, m).

EXAMPLE 7

Methyl 9α,11α-dimercapto-15α-hydroxyprosta-cis-5,trans-13-dienoate

[(5Z,9α,11α,13E,15S)-9,11-dimercapto-15-hydroxy-prosta-5,13-dienoic acid methyl ester]

By proceeding as described in Example 3, but using 70 mg. of methyl 9α,11α-dimercapto-15α-(2-tetrahydropyranyloxy)-prosta-cis-5,trans-13-dienoate (prepared as described in Example 4) there were obtained 30 mg. of the title compound having the following physical characteristics:

TLC:
(i) developing solvent (cyclohexane — ethyl acetate = 2:1): Rf = 0.42 (tailing);
(ii) developing solvent (chloroform — ethanol = 20:1): Rf = 0.59;

IR (liquid film): ν; 3450, 3020, 2940, 2860, 2560, 1740, 1430, 1360, 1270, 1170, 1020, 970 cm$^{-1}$;

NMR (CDCl$_3$ solution): δ; 5.84–5.10 (4H, m), 4.25–3.90 (1H, m), 3.67 (3H, s), 3.80–3.15 (1H, m), 3.15–2.55 (1H, m), 1.88 (1H, d), 1.58 (1H, d).

EXAMPLE 8

Methyl 9β,11β-dimercapto-15α-hydroxyprosta-cis-5,trans-13-dienoate

[(5Z,9β,11β,13E,15S)-9,11-dimercapto-15-hydroxy-prosta-5,13-dienoic acid methyl ester]

A solution of 156 mg. of methyl 9β,11β-dimercapto-15α-(2-tetrahydropyranyloxy)prosta-cis-5,trans-13-dienoate (prepared as described in Example 1) in a mixture of 0.5 ml. of tetrahydrofuran, 7.25 ml. of acetic acid, and 1.75 ml. of water was stirred at 40° C. for one hour, the reaction mixture poured into 50 ml. of water, and extracted with ethyl acetate. The extract was washed with an aqueous solution of sodium bicarbonate and an aqueous solution of sodium chloride, dried over magnesium sulphate and concentrated under reduced pressure. The residue was purified by column chromatography on silica gel using a mixture of cyclohexane and ethyl acetate (6:1) as eluent to give 88 mg. of the title compound having the following physical characteristics:

TLC (developing solvent cyclohexane-ethyl acetate = 2:1):
Rf = 0.27;

NMR (CDCl$_3$ solution): δ; 5.83–5.70 (4H, m), 4.23–3.08 (1H, m), 3.65 (3H, s), 3.45–3.15 (1H, m), 2.82–2.60 (1H, m), 2.60–1.05 (24H, m), 0.90 (3H, t).

What we claim is:

1. A compound of the formula:

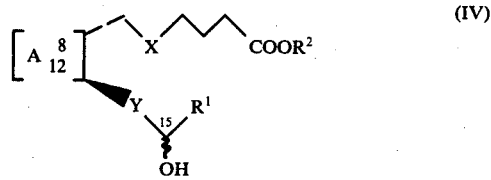

wherein A represents a grouping of the formula:

or

X represents ethylene or cis-vinylene, Y represents ethylene or trans-vinylene, R$^1$ represents a straight- or branched-chain alkyl group containing from 4 to 10 carbon atoms, and R$^2$ represents a hydrogen atom or a straight- or branched-chain alkyl group containing from 1 to 12 carbon atoms and cyclodextrin clathrates of such acids and esters and, when R$^2$ represents a hydrogen atom, non-toxic salts thereof, the bonds attaching the epidithio radical to the carbon atoms in the 9- and 11- positions in the grouping of formula VA being either both in α-configuration or both in β-configuration.

2. A compound according to claim 1 wherein $R^1$ represents n-pentyl.

3. A compound according to claim 1 wherein X represents cis-vinylene.

4. A compound according to claim 1 wherein Y represents trans-vinylene.

5. A compound according to claim 1 wherein $R^2$ represents a hydrogen atom or a straight- or branched-chain alkyl group containing from 1 to 4 carbon atoms.

6. A compound according to claim 1 wherein $R^2$ represents methyl.

7. A compound according to claim 1 wherein the hydroxy group attached to the C-15 carbon atom of formula IV depicted in claim 1 is in α-configuration.

8. A compound according to claim 1 which is methyl 9α,11α-dimercapto-15α-hydroxyprosta-cis-5,trans-13-dienoate.

9. A compound according to claim 1 which is methyl 9β,11β-dimercapto-15α-hydroxyprosta-cis-5,trans-13-dienoate.

10. A compound according to claim 1 which is methyl 9α,11α-epidithio-15α-hydroxyprosta-cis-5,trans-13-dienoate.

11. A compound according to claim 1 which is methyl 9β,11β-epidithio-15α-hydroxyprosta-cis-5,trans-13-dienoate.

* * * * *